(12) United States Patent
Brasier et al.

(10) Patent No.: US 11,389,433 B2
(45) Date of Patent: Jul. 19, 2022

(54) BRD4 INHIBITOR TREATMENT OF IGE-MEDIATED DISEASES

(71) Applicant: THE BOARD OF REGENTS OF THE UNIVERSITY OF TEXAS SYSTEM, Austin, TX (US)

(72) Inventors: Allan Brasier, Galveston, TX (US); Sanjiv Sur, Galveston, TX (US); Jia Zhou, Galveston, TX (US); Bing Tian, Galveston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/444,698

(22) Filed: Jun. 18, 2019

(65) Prior Publication Data
US 2019/0381013 A1    Dec. 19, 2019

Related U.S. Application Data

(60) Provisional application No. 62/686,366, filed on Jun. 18, 2018.

(51) Int. Cl.
*A61K 31/438* (2006.01)
*A61K 45/06* (2006.01)

(52) U.S. Cl.
CPC ............ *A61K 31/438* (2013.01); *A61K 45/06* (2013.01)

(58) Field of Classification Search
CPC .............................. A61K 31/438; A61K 45/06
See application file for complete search history.

(56) References Cited

U.S. PATENT DOCUMENTS

| | | | |
|---|---|---|---|
| 4,668,218 | A | 5/1987 | Virtanen |
| 5,458,135 | A | 10/1995 | Patton et al. |
| 6,488,953 | B2 | 12/2002 | Halliday et al. |
| 6,737,045 | B2 | 5/2004 | Patton et al. |
| 6,794,357 | B1 | 9/2004 | Backstrom |
| 6,797,258 | B2 | 9/2004 | Platz et al. |
| 2011/0236437 | A1 | 9/2011 | Destache |
| 2015/0148344 | A1 | 5/2015 | Babaoglu et al. |

FOREIGN PATENT DOCUMENTS

| | | |
|---|---|---|
| EP | 0237507 | 9/1987 |
| WO | WO 94/06498 | 3/1994 |
| WO | WO 94/08552 | 4/1994 |
| WO | WO 94/16970 | 8/1994 |
| WO | WO 97/25086 | 7/1997 |
| WO | WO 98/35888 | 8/1998 |
| WO | WO 2014/159837 | 10/2014 |

OTHER PUBLICATIONS

Brook et al., European Respiratory Journal, 2014;44(Suppl 58):4862 (Year: 2014).*
Pease et al., Am J Respir Med., 2002;1(1):19-25 (Year: 2002).*
Lloyd et al., Eur Respir J, 2007;29(5):1020-1032 (Year: 2007).*

(Continued)

*Primary Examiner* — San Ming R Hui

(57) ABSTRACT

Certain embodiments are directed to methods of using BRD4 inhibitors for treating IgE-mediated diseases.

8 Claims, 15 Drawing Sheets

(56) References Cited

OTHER PUBLICATIONS

Alexopoulou et al., "Recognition of double-stranded RNA and activation of NF-κB by Toll-like receptor 3," *Nature*, 413(6857); 732-738, 2001.
Bisgrove et al., "Conserved P-TEFb-Interacting Domain of BRD4 Inhibits HIV Transcription," *PNAS USA*, 104(34); 13690-13695, 2007.
Brasier, et al., "ReIA Ser276 Phosphorylation-Coupled Lys310 Acetylation Controls Transcriptional Elongation of Inflammatory Cytokines in Respiratory Syncytial Virus Infection," *Journal of Virology*, 85(22); 11752-69, 2011.
Brown, et al., NF-κB Directs Dynamic Super Enhancer Formation in Inflammation and Atherogenesis, *Molecular Cell*, 56(2); 219-231, 2014.
Burke et al., "BMS-345541 Is a Highly Selective Inhibitor of IkB Kinase That Binds at an Allosteric Site of the Enzyme and Blocks NF-κB-dependent Transcription in Mice," *Journal of Biological Chemistry*, 278(3); 1450-1456, 2003.
Creticos, et al., "Nasal Challenge with Ragweed Pollen in Hay Fever Patients Effect of Immunotherapy," *The Journal of Clinical Investigation*, 76(6); 2247-2253, 1985.
Creticos, et al., "Peptide Leukotriene Release After Antigen Challenge in Patients Sensitive to Ragweed," *New England Journal of Medicine*, 310(25); 1626-1630, 1984.
De Boer et al., "Altered Expression of Epithelial Junctional Proteins in Atopic Asthma: Possible Role in Inflammation," *Canadian Journal of Physiology and Pharmacology*, 86(3); 105-112, 2008.
Ding et al., "BRD4 is a Novel Therapeutic Target for Liver Fibrosis," *PNAS*, 112(51); 15713-15718, 2015.
Filippakopoulos, et al., "Selective Inhibition of BET Bromodomains," *Nature*, 468(7327); 1067-1073, 2010.
Fitzgerald, et al., "LPS-TLR4 Signaling IRF-3/7 and Nf-kB Involved the Toll Adapters TRAM and TRIF," *Journal of Experimental Medicine*, 198(7); 1043-1055, 2003.
Fransson, et al., "A Role for Neutrophils in Intermittent Allergic Rhinitis," *Acta Otolaryngologica*, 124(5); 616-620, 2004.
Galdeano and Ciulli, "Selectivity on-Target of Bromodomain Chemical Probes by Structure-Guided Medicinal Chemistry and Chemical Biology," *Future Medicinal Chemistry*, 8(13); 1655-1680, 2016.
Ghoshal et al., "BET Inhibitors in Cancer Therapeutics: A Patent Review," *Expert Opinion Therapeutic Patents*, 26; 505-522, 2016.
Greer et al., "Mass Spectrometry Imaging for Drugs and Metabolites," *Journal of Proteomics*, 74(12); 2617-2631, 2011.
Holgate et al., "Epithelial-Mesenchymal Communication in the Pathogenesis of Chronic Asthma," *Proceedings of the American Thoracic Society*, 1(2); 93-8, 2004.
Hosoki, et al., "Facilitation of Allergic Sensitization and Allergic Airway Inflammation by Pollen-Induced Innate Neutrophil Recruitment," *American Journal of Respiratory Cell and Molecular Biology*, 54(1); 81-90, 2016.
Hosoki, et al., "Myeloid Differentiation Protein 2 Facilitates Pollen—And Cat Dander-Induced Innate and Allergic Airway Inflammation," *The Journal of Allergy and Clinical Immunology*, 137(5); 1506-1513, e2, 2016.
Hosoki, et al., "Innate Mechanism of Pollen- and Cat Dander-Induced Oxidative Stress and DNA Damage in the Airways," *The Journal of Allergy and Clinical Immunology*, 140(6); 1436-1439, 2017.
Hruska et al., "Effects of Ribavirin on Respiratory Syncytial Virus in Vitro," *Antimicrobial Agents and Chemotherapy*, 17(5);770-775, 1980.
Huang et al., "Junin Virus Infection Activates the Type I Interferon Pathway in a RIG-I-Dependent Manner," *PLoS Neglected Tropical Diseases*, 6(5); e1659, pp. 1-10, 2012.
Huang et al., "Early Events in Cell Adhesion and Polarity During Epithelial-Mesenchymal Transition," *Journal of Cell Science*, 125(19); 4417-4422, 2012.
Huber et al., "Epithelial-Mesenchymal Transition: NF-κB Takes Center Stage," *Cell Cycle*,3(12); 1477-1480, 2004.

Huber et al., "NFκB Is Essential for Epithelial-Mesenchymal Transition and Metastasis in a Model of Breast Cancer Progression," *Journal of Clinical Investigation*, 114(4);569-581, 2004.
Ijaz et al., "Systems Biology Approaches to Understanding Epithelial Mesenchymal Transition (EMT) in Mucosal Remodeling and Signaling in Asthma," *World Allergy Organization Journal*, 7(1);13, 2014.
International Preliminary Report on Patentability Issued in Corresponding PCT Application No. PCT/US2017/066107, dated Jun. 18, 2019.
International Search Report and Written Opinion Issued in Corresponding PCT Application No. PCT/US2017/066107, dated Apr. 24, 2018.
Jang, et al., "The Bromodomain Protein Brd4 is a Positive Regulatory Component of P-TEFb and Stimulates RNAPolymerase II-Dependent Transcription," *Molecular Cell*, 19(4); 523-534, 2005.
Kalita et al., "Systems Approaches to Modeling Chronic Mucosal Inflammation," *Biomedical Research International*, Article 505864, 2013.
Kalluri and Weinberg, "The Basics of Epithelial-Mesenchymal Transition," *Journal of Clinical Investigation*, 119(6);1420-28, 2009.
Kaltenborn, et al., "Respiratory Syncytial Virus Potentiates ABCA3 Mutation-Induced Loss of Lung Epithelial Cell Differentiation," *Human Molecular Genetics*, 21(12); 2793-2806, 2012.
Kanno, et al., "BRD4 Assist Elongation of Both Coding and Enhancer RNAs by Interacting with Acetylated Histones," *Nature Structural & Molecular Biology*, 21(12);1047-57, 2014.
Kim, et al., "Constitutively Active Type I Insulin-Like Growth Factor Receptor Causes Transformation and Xenograft Growth of Immortalized Mammary Epithelial Cells and is Accompanied by an Epithelial-to-Mesenchymal Transition Mediated by NF-κB and Snail," *Molecular and Cellular Biology*, 27(8); 3165-3175, 2007.
Korb et al., "BET Protein BRD4 Activates Transcription in Neurons and BET Inhibitor Jq1 Blocks Memory in Mice," *Nature Neuroscience*, 18; 1464-73, 2015.
Korkaya, et al., "Activation of an IL6 Inflammatory Loop Mediates Trastuzumab Resistance in HER2+ Breast Cancer by Expanding the Cancer Stem Cell Population," *Molecular Cell*, 47; 570-584; 2012.
Lai et al., "Inhibition of Respiratory Syncytial Virus Infections with Morpholino Oligomers in Cell Cultures and in Mice," *Molecular Therapy*, 16(6); 1120-1128, 2008.
Lambrecht et al., "The Airway Epithelium in Asthma," *Nature Medicine*, 18(5); 684-692, 2012.
Leaman, et al., "Targeted Therapy of Respiratory Syncytial Virus in African Green Monkeys by Intranasally Administered 2-5A Antisense," *Virology*, 292(1); 70-77, 2002.
Li et al., "Epithelial-Mesenchyme Transition Induced by TNF-α Requires NF-κB -Mediated Transcriptional Upregulation of Twist1," *Cancer Research*, 72(5); 1290-1300, 2012.
Li, et al., "The BET Bromodomain Inhibitor JQ1 Activates HIV Latency Through Antagonizing BRD4 Inhibition of Tat-Transactivation," *Nucleic Acids Research*, 41; 277-287, 2013.
Lietz, et al., "Qualitative and Quantitative Mass Spectrometry Imaging of Drugs and Metabolites," *Advanced Drug Delivery Review*, 65(8); 1074-1085, 2013.
Liu et al., "Drug Discovery Targeting Bromodomain-Containing Protein 4," *Journal of Medicinal Chemistry*, 60(11); 4533-4558, 2017.
Liu et al., "Retinoic Acid-Inducible Gene I Mediates Early Antiviral Response and Toll-Like Receptor 3 Expression in Respiratory Syncytial Virus-Infected Airway Epithelial Cells," *Journal of Virology*, 81(3);1401-1411, 2007.
McDonald et al., "Genome-Scale Epigenetic Reprogramming During Epithelial-To-Mesenchymal Transition," *Nature Structural & Molecular Biology*, 18; 867-874, 2011.
Miadonna, et al., "Nasal Response to a Single Antigen Challenge in Patients with Allergic Rhinitis—Inflammatory Cell Recruitment Persists Up To 48 Hours," *Clinical and Experimental Allergy*, 29(7); 941-949, 1999.
Naclerio, et al., "Mediator Release After Nasal Airway Challenge with Allergen," *American Review of Respiratory Disease*, 128(4); 597-602, 1983.

(56) References Cited

OTHER PUBLICATIONS

Nicholls, et al., "ApoA-I Induction as a Potential Cardioprotective Strategy: Rationale for the SUSTAIN and ASSURE Studies," *Cardiovascular Drugs and Therapy*, 26; 181-187, 2012.

Nowak et al., "ReIA Ser276 Phosphorylation is Required for Activation of a Subset of NF-κB-Dependent Genes by Recruiting Cyclin-Dependent Kinase 9/Cyclin T1 Complexes," *Molecular and Cellular Biology*, 28(11); 3623-3638, 2008.

Nowak et al., "Two-Step Cross-Linking Method for Identification of NF-κB Gene Network by Chromatin Immunoprecipitation," *Biotechniques*, 39(5):715-725, 2005.

Pelikan, "Cytological Changes in Nasal Secretions Accompanying Delayed Nasal Response to Allergen Challenge," *American Journal of Rhinology & Allergy*, 27(5); 345-353, 2013.

Peters-Golden, et al., "Cysteinyl Leukotrienes: Multi-functional Mediators in Allergic Rhinitis," *Clinical and Experimental Allergy*, 36(6); 689-703, 2006.

Pubchem 45582977 created on Jun. 21, 2010, pp. 1-10, p. 3 Retrieved from https://pubchem.ncbi.nlm.nih.gov/compound/45582977.

Ramirez, et al., "Immortalization of Human Bronchial Epithelial Cells in the Absence of Viral Oncoproteins," *Cancer Research*, 64(24); 9027-9034, 2004.

Rytting et al., "Biodegradable Polymeric Nanocarriers for Pulmonary Drug Delivery," *Expert Opinion on Drug Delivery*, 5(6); 629-639, 2008.

Sagara, et al., "Activation of TGF-Beta/Smad2 Signaling is Associated with Airway Remodeling in Asthma," *Journal of Allergy and Clinical Immunology*, 110(2); 249-54, 2002.

Tian, et al., "Analysis of the TGFβ-Induced Program in Primary Airway Epithelial Cells Shows Essential Role of NF-κB/ReIA Signaling Network in Type II Epithelial Mesenchymal Transition," 2015, *BMC Genomics*, 16; 529, 2015.

Tian, et al., "BRD4 Mediates NF-κB-Dependent Epithelial-Mesenchymal Transition and Pulmonary Fibrosis Via Transcriptional Elongation," *American Journal of Physiology Lung Cellular and Molecular Physiology*, 311(6), 2016.

Tian, et al., "CDK9-Dependent Transcriptional Elongation in the Innate Interferon-Stimulated Gene Response to Respiratory Syncytial Virus Infection in Airway Epithelial Cells," *Journal of Virology*, 87(12); 7075-7092, 2013.

Tian, et al., "Identification of Direct Genomic Targets Downstream of the Nuclear Factor-κB Transcription Factor Mediating Tumor Necrosis Factor Signaling," *Journal of Biological Chemistry*, 280(17); 17435-17448, 2005.

Tian, et al., "Selective Antagonists of the Bronchiolar Epithelial NF-κB-Bromodomain-Containing Protein 4 Pathway in Viral-Induced Airway Inflammation," Cell Reports, 23; 1138-1151, 2018.

Tian, et al., "Two-Step Cross-Linking for Analysis of Protein-Chromatic Interactions," *Methods. Mol. Biol.* 809:105-120, 2012.

Wu and Chiang, "The Double Bromodomain-Containing Chromatin Adaptor BRD4 and Transcriptional Regulation," *Journal of Biological Chemistry*, 282(18); 13141-13145, 2007.

Xu & Vakoc, "Brd4 Is On The Move During Inflammation," *Trends in Cell Biology*, 24(11); 615-616, 2014.

Yang, et al., "The 7SK Small Nuclear RNA Inhibits the CDK9/Cyclin T1 Kinase to Control Transcription," *Nature*, 414(6861); 317-322, 2001.

Zhang, et al., "Discovery of Chemical Inhibitors of Human Bromodomains," *Chemical Review*, 115(121); 11625-11668, 2015 (Figure 7).

Zhao, et al., "Quantification of Activated NF-κB/ReIA Complexes Using ssDNA Aptamer Affinity—Stable Isotope Dilution—Selected Reaction Monitoring—Mass Spectrometry," *Molecular & Cellular Proteomics*, 10(6); M111, 2011.

Zhao, et al., "Quantitation of the Dynamic Profiles of the Innate Immune Response Using Multiplex Selected Reaction Monitoring—Mass Spectrometry," *Molecular & Cellular Proteomics*, 12(6); 1513-1529, 2013.

Zou, et al., "BRD4 Maintains Constitutively Active NF-κB in Cancer Cells by Binding to Acetylated RelA," *Oncogene*, 33; 2395-2404, 2014.

* cited by examiner

BRD4 INHIBITOR TREATMENT OF IGE-MEDIATED DISEASES

PRIORITY STATEMENT

The present application claims priority to U.S. Application No. 62/686,366 filed Jun. 18, 2018, which is incorporated herein by reference in its entirety.

STATEMENT REGARDING FEDERALLY FUNDED RESEARCH

None.

BACKGROUND

Allergen-induced airway remodeling[1] functionally impacts the quality of life for over 300 million patients with asthma[2-4]. Intrinsic proteolytic enzymes and NADPH-oxidase activities intrinsic to aeroallergens[5,6] trigger mucosal innate signaling downstream of toll-like receptors (TLRs) and protease-activated receptors (PARs)[7-9]. The innate pathway produces coordinate disruption of the mucosal barrier function and activates dendritic cell (DC) recruitment, leading to enhanced antigen penetration, Th2 polarization, and IgE production[10]. Consequently allergic sensitization produces a stable submucosal population of Th2 lymphocytes producing fibrogenic cytokines leading to epithelial barrier dysfunction, goblet cell metaplasia, and mucosal thickening. Despite this understanding, the mechanisms for how allergen-induced innate signaling in the mucosa cause remodeling is not completely understood.

Cat dander is one of the most prevalent indoor house aeroallergens. In large scale epidemiological studies, cat dander sensitization is associated with asthma in ~29% of individuals[11] and is found in household dust at levels far above that necessary to induce an IgE response[12]. In unsensitized airways, acute cat dander exposure (CDE) is a potent innate inflammatory stimulus, mediated by binding the epithelial TLR4-MD2 complex independent of LPS signaling pathways[5,6]. Downstream, the IKK-NFκB pathway is activated, resulting in oxidative DNA damage, CXCL2 expression, and neutrophil recruitment[13]. The mechanisms of how these acute inflammatory responses disrupt epithelial barrier and/or airway remodeling are not fully understood. Recently, the inventors have identified a molecular link between epithelial TLR3 stimulation, NFκB activation, and airway remodeling[14-16]. These studies demonstrated the central role of NFκB in controlling a coordinate phenotypic transition of the epithelial cells to undergo type II epithelial mesenchymal transition (EMT)[14,17,18]. The mechanisms how NFκB mediates allergen-induced sensitization and airway remodeling downstream of TLR4 are still unknown.

Frequent exacerbations of allergic asthma leads to airway remodeling and progressive decline in pulmonary function, a source of significant morbidity and mortality. Thus, there remains a need for additional methods for treating or ameliorating IgE-mediated diseases in subjects in need thereof.

SUMMARY

Certain embodiments are directed to methods of using BRD4 inhibitors for treating IgE-mediated diseases. In bronchial specimens of allergic asthmatic, such as that brought about by cat dander exposure (CDE), the inventors detected gene expression signatures of EMT and mesenchymal growth factors. A mouse model was established to study the mechanisms underlying the effects of repeated, chronic exposure to cat dander. The inventors found that repetitive mucosal CDE (rCDE) exposures induce EMT, interstitial fibrosis, and expansion of the pro-fibrogenic myofibroblast population mediated through the IKK-NFκB/RelA pathway. rCDE induces RelA to complex and activate the BRD4 atypical histone acetyltransferase (HAT). The results presented herein validate the BRD4 epigenetic reader as a therapeutic target to prevent airway remodeling and allergic sensitization. The inventors have identified potent highly selective small molecule inhibitors of BRD4[19] that prevent EMT, mucous metaplasia, myofibroblast expansion, and fibrosis. Thus it was contemplated that administration of a BRD4 inhibitor could be used as a treatment for a variety of IgE-mediated diseases.

Certain embodiments are directed to methods for treating or ameliorating an IgE-mediated disease comprising administering to a subject having or at risk of developing an IgE-mediated disease an effective amount of a small molecule BRD4 inhibitor. In certain aspects the small molecule BRD4 inhibitor is administered at 0.1 to 100 mg/kg body weight.

Other embodiments are directed to methods for treating or ameliorating allergic rhinitis (AR) comprising administering to a subject having or at risk of developing allergic rhinitis (AR) an effective amount of a BRD4 inhibitor. In certain aspects the small molecule BRD4 inhibitor is administered at 0.1 to 100 mg/kg body weight.

Still other embodiments are directed to methods for treating or ameliorating allergic asthma or severe asthma with elevated IgE comprising administering to a subject having or at risk of developing allergic asthma or severe asthma with elevated IgE an effective amount of a BRD4 inhibitor. In certain aspects the small molecule BRD4 inhibitor is administered at 0.1 to 100 mg/kg body weight.

Certain embodiments are directed to methods for treating or ameliorating chronic idiopathic urticarial (CIU) atopic dermatitis (eczema) or angioedema comprising administering to a subject having or at risk of developing chronic idiopathic urticarial (CIU) atopic dermatitis (eczema) or angioedema an effective amount of a BRD4 inhibitor. In certain aspects the small molecule BRD4 inhibitor is administered at 0.1 to 100 mg/kg body weight.

Other embodiments are directed to methods for treating or ameliorating recurrent IgE-mediated anaphylaxis comprising administering to a subject having or at risk of developing recurrent IgE-mediated anaphylaxis an effective amount of a BRD4 inhibitor. In certain aspects the small molecule BRD4 inhibitor is administered at 0.1 to 100 mg/kg body weight.

Still other embodiments are directed to methods for treating or ameliorating mast cell activation disorders and systemic mastocytosis comprising administering to a subject having or at risk of developing mast cell activation disorders and systemic mastocytosis an effective amount of a BRD4 inhibitor. In certain aspects the small molecule BRD4 inhibitor is administered at 0.1 to 100 mg/kg body weight.

Certain embodiments are directed to methods for treating or ameliorating systemic eosinophilic esophagitis, oral food allergy comprising administering to a subject having or at risk of developing systemic eosinophilic esophagitis, oral food allergy an effective amount of a BRD4 inhibitor. In certain aspects the small molecule BRD4 inhibitor is administered at 0.1 to 100 mg/kg body weight.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention.

Throughout this application, the term "about" is used to indicate that a value includes the inherent variation of error for the device, the method being employed to determine the value, or the variation that exists among the study subjects.

The terms "comprise," "have," and "include" are open-ended linking verbs. Any forms or tenses of one or more of these verbs, such as "comprises," "comprising,", "has," "having," "includes," and "including," are also open-ended. For example, any method that "comprises," "has," or "includes" one or more steps is not limited to possessing only those one or more steps and also covers other unlisted steps.

As used herein, the term "$IC_{50}$" refers to an inhibitory dose that results in 50% of the maximum response obtained.

The term half maximal effective concentration ($EC_{50}$) refers to the concentration of a drug that presents a response halfway between the baseline and maximum after some specified exposure time.

The terms "inhibiting", "reducing", or "prevention", or any variation of these terms, when used in the claims and/or the specification includes any measurable decrease or complete inhibition to achieve a desired result.

The use of the term "or" in the claims is used to mean "and/or" unless explicitly indicated to refer to alternatives only or the alternatives are mutually exclusive, although the disclosure supports a definition that refers to only alternatives and "and/or."

As used herein, the term "patient" or "subject" refers to a living mammalian organism, such as a human, monkey, cow, sheep, goat, dogs, cat, mouse, rat, guinea pig, or species thereof. In certain embodiments, the patient or subject is a primate. Non-limiting examples of human subjects are adults, juveniles, infants and fetuses.

The use of the word "a" or "an" when used in conjunction with the term "comprising" in the claims and/or the specification may mean "one", but it is also consistent with the meaning of "one or more", "at least one", and "one or more than one".

DESCRIPTION OF THE DRAWINGS

The following drawing forms part of the present specification and is included to further demonstrate certain aspects of the present invention. The invention may be better understood by reference to one or more of these drawings in combination with the detailed description of the specification embodiments presented herein.

DESCRIPTION

The airway epithelium is the first line of defense against allergens and plays important roles in sensitization, the process of developing IgE to plant or animal aeroallergens. The inventors have investigated the mechanisms through which animal aeroallergens induce sensitization. The inventors show that ragweed pollen extract (RWPE) and cat dander extract (CDE) stimulate recruitment of reactive oxygen species (ROS)-generating neutrophils to the lungs of mice, and these neutrophils together with allergens stimulate allergic sensitization and inflammation[68, 69] as well as TLR4-dependent ROS and oxidative DNA damage[70].

Repetitive exposure to CDE produces acute inflammation, epithelial barrier dysfunction, airway remodeling, and chronic IgE production. IgE is a major effector of AR and allergic asthma that is on the surface of mast cells. The exposure of allergens cross-links IgE on mast cells, stimulating histamine release and causing immediate nasal symptom. This is followed by infiltration by inflammatory cells such as neutrophils, eosinophils, and T-cells into nasal mucosal tissue that results in the late-phase allergic response[71-74].

As demonstrated in the examples provided below, the inventors have established a murine model of repetitive cat dander exposure, observed that cat dander exposure induces NFκB/RelA to complex with—and activate the chromatin reader, bromodomain-containing protein 4 (BRD4), to become an epigenetic regulator responsible for activating RNA Pol II and remodeling of inflammatory and fibrogenic genes through its atypical histone acetyltransferase (HAT) activity. The inventors also demonstrate that small-molecule BRD4 inhibitors (e.g., ZL0454) disrupts BRD4 binding to the NFκB-RNA Pol II complex and inhibits its HAT activity.

Figure 14:
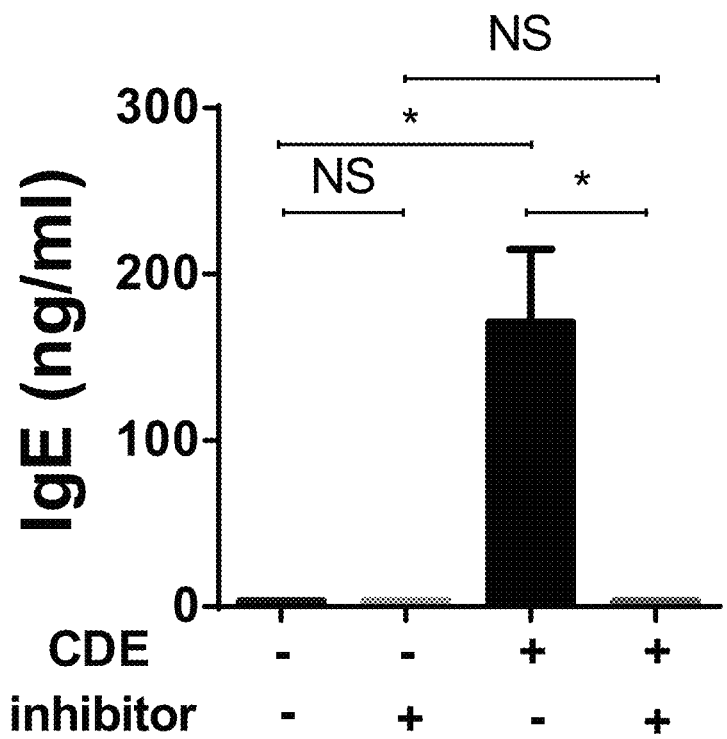
FIG. 14. Effect of BRD4 inhibitor in blocking allergic sensitization. Serum IgE levels were measured in mice after treatment with repetitive airway exposures to cat dander extract (CDE). *, $p<0.01$; NS, not significant.
Figure 15:
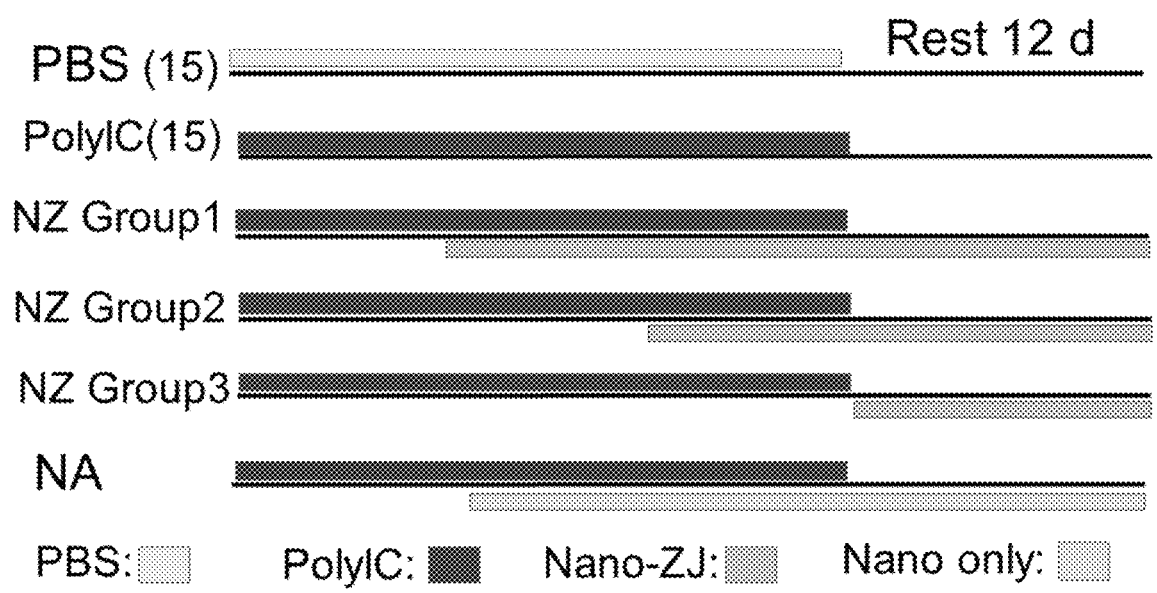
FIG. 15. Experimental design of the effect of Nanoparticle-encapsulated BRD4 inhibitor on reversal of airway fibrosis. In this design, there are 6 experimental groups (n=6). Among these 6 groups, One group of mice received only PBS intranasally and while other 5 groups of C57BL/6 mice were treated with poly(I:C) for total 15 times every other day. The mice administered intranasally with Nanoparticle-encapsulated BRD4 inhibitor PLGA-ZL0420 (NZ, 2 mg/kg body weight) daily were divided into three groups: (a). NZ group 1; NZ were given after 5 administrations of poly(I:C); (b). NZ group 2; NZ were given after 10 administrations of poly(I:C); (c). NZ group 3; NZ were given after 15 administrations of poly(I:C): Also, the blank nanoparticle PLGA-ZL0420 (NA) were given intranasally after 5 administrations of poly(I:C) as the control for the other 4 poly(I:C)-treated groups. Mice of all experimental groups were harvested 12 d after last poly(I:C) challenge for analysis of fibrosis levels, and collagen deposition, and fibrogenic gene program in lung tissues as shown in FIG. 16. NZ: Nanoparticle-encapsulated BRD4 inhibitor PLGA-ZL0420, NA: blank nanoparticles PLGA-ZL0420.
Figure 16:
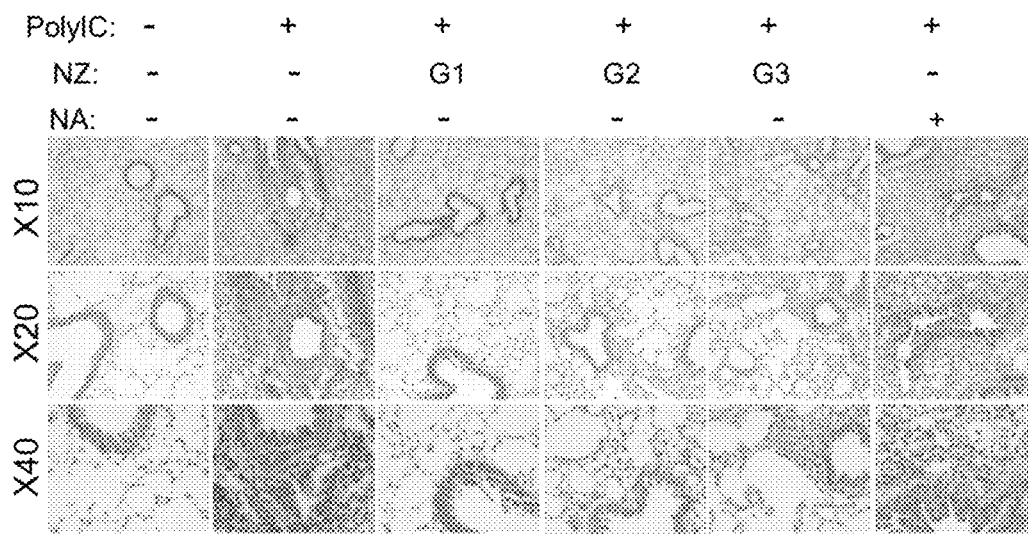
FIG. 16. Effect of the PLGA-ZL0420 on reversal of airway fibrosis. (A). Histological assessment of airway fibrosis. Masson's Trichrome staining of representative lung section at 10×, 20×, and 40× magnification as indicated. Note the epithelial barrier disruption, myofibroblast expansion and collagen (blue) deposition in the subepithelial and interstitial space in the poly(I:C) treated group that is largely reversed by the Nanoparticle-encapsulated PLGA-ZL0420 at NZ group 1. (B). Modified Ashcroft scoring for treatment groups. n=6 in each group. (C). Hydroxyproline content of bronchoalveolar lavage (BALF). Shown is mean hydroxyproline measurement for BALF from n=6 mice in each group. (D). Hydroxyproline content of lung tissue. n=6 in each group. (E). Nanoparticle PLGA-ZL0420 fibrogenic gene program of lung tissue. Total lung RNA was extracted, purified, and reverse transcribed. The abundance of indicated mRNAs was determined using mouse gene-selective primers. Shown is mean fold change mRNA abundance (±SD) normalized to mouse cyclophilin (mPPIA). **, $p<0.01$, *, $p<0.05$ compared to poly(I:C) only treated controls; ##, $p<0.01$ compared to PBS only treated mice. n=6 in each group.
Figure 16:
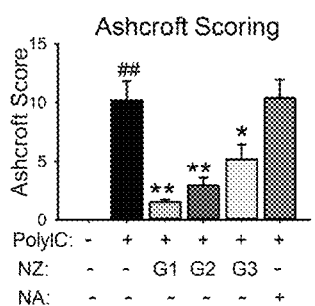
Figure 16:
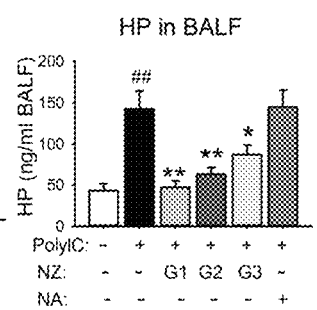
Figure 16:
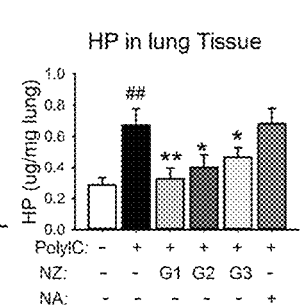
Figure 16:
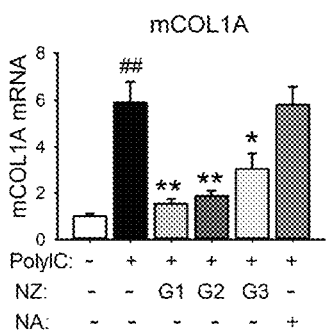
Figure 16:
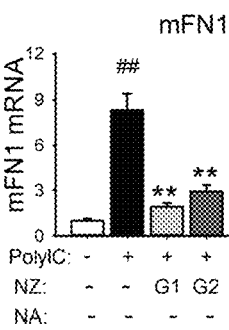
Figure 16:
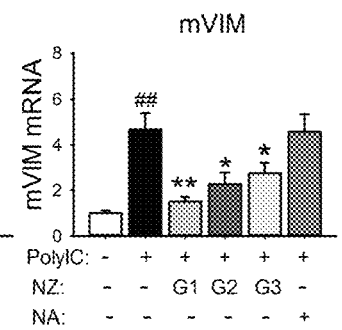

BRD4 inhibitors (e.g., ZL0454) prevent IgE sensitization in cat dander-exposed mice (FIG. 14). In contrast to the dramatic induction of CDE-specific IgE, mice treated with ZL0454 have completely blunted allergic responses. These studies indicate that the NFκB-inducible BRD4 activity is an epigenetic regulator of aeroallergen sensitization.

The discovery that BRD4 inhibitors block allergic sensitization (IgE) formation indicates that mucosal BRD4 inhibitors are be first in class drugs that would block allergic sensitization per se.

Small molecule BRD4 inhibitors have a distinct mechanism of action from currently therapies targeting IgE-mediated diseases, e.g., OmAb, and less expensive than current antibody-based therapeutics.

I. IGE-MEDIATED DISEASES

Immunoglobulin E (IgE) is a unique isotype of immunoglobulin that mediates the pathophysiology of allergic reactions. In response to exposure, allergenic proteins are processed by CD4+ Th2 cells, which stimulate B-cell production of IgE antibodies that are also antigen-specific. Upon subsequent exposure to the sensitized allergen, IgE binds, and activates specialized "effector cells", mast cells and basophils by cross-linking a high affinity, membrane receptor FcεRI. This binding releases vasoactive products, such as histamines, serotonin, and inflammation-related cytokines[55-58]. Depending on the route of exposure, this allergic response produces cough, bronchospasm, wheezing, in the airways, diarrhea in the intestines, and wheals/edema in the skin[59]. The importance of each of these IgE mediated diseases are briefly described below:

Allergic Rhinitis (AR).

The NHANES III epidemiologic study discovered that 30% of the US population have AR[60-62]. One US study calculated the workplace productivity loss from AR was about $593 per employee per year, and this translates into a staggering loss of about $66 billion per year for the entire work force[63]. Thus there is very high morbidity from AR, and there is a strong market for cost-effective therapies that affect the underlying disease.

Allergic Asthma.

Asthma is a heterogenous inflammatory disease of the airways affecting approximately 26 million people in the US and 300 million people worldwide[64]. A subtype of asthma is associated with Th2-driven inflammation, associated with eosinophils and IgE[65], a subtype that constitutes up to 50% of asthmatics. Allergic asthma is linked with other allergic diseases such as allergic rhinitis and atopic dermatitis. Exposure to allergens triggers an acute inflammatory disease resulting in an exacerbation of disease. These asthma attacks constitute a considerable part of the disease burden in terms of both personal suffering and economic impact. Exacerbations are characterized in part by decreases in expiratory flow or lung function, and result in unscheduled medical visits. Exacerbations also result in decreased quality of life—the prevention of which are the major focus of medical interventions[66].

Chronic Idiopathic Urticaria (CU).

CU is a skin disease characterized by wheals that develop quickly with a central edema and a surrounding area of erythema. The size of the wheals is variable and the lesions last from one to 24 hours. The disease may be accompanied by angioedema, defined as cutaneous or mucosal swelling that is generally nonpruritic but is painful and lasts from one to three days. Urticaria can be divided into two groups on the basis of its clinical manifestations: the acute form, which lasts less than six weeks and is often allergic, and chronic spontaneous urticaria (CSU), also known as chronic spontaneous/idiopathic urticaria, which presents daily or almost daily wheals for more than six weeks. This condition affects 0.1%-0.8% of the population. Chronic spontaneous urticaria may occur as a result of mast cell and basophil release of bioactive mediators.

Atopic Dermatitis (AD).

AD is one of the most frequent chronic inflammatory skin disorders associated with elevated serum IgE levels.

Food Allergy.

Food allergy is a common disease with an estimated prevalence of 6-8% in childhood[67]. Food allergies are typically to proteins ingested in the diet. Although most allergies to cow's milk, egg, soybean and wheat are outgrown, allergies to peanut, tree nuts, seeds and seafood persist into adulthood. High levels of IgE antibodies to cow's milk, egg white, wheat and soy are associated with persistent food allergy. Clinical manifestations include oral allergy, systemic anaphylaxis, or abdominal pain/dysphagia. Although some Eosinophilic esophagitis.

II. BRD4 INHIBITORS

The bromodomain protein BDR4 is a chromatin remodeling enzyme recognized as one of the most important regulators of immune responses (Filippakopoulos et al., *Nature*, 2010, 468(7327):1067-73; Xu and Vakoc, *Trends Cell Biol*, 2014, 24(11):615-16; Brown et al., *Mol Cell*, 2014, 56(2):219-31; Kanno et al., *Nat Struct Mol Biol*, 2014, 21(12):1047-57). The bromodomain and extraterminal domain (BET) family proteins (Wu and Chiang, *J Biol Chem*, 2007, 282(18):13141-45), including BRD2, BRD3, BRD4 and BRDT, contain two bromodomains (BDs) (Filippakopoulos et al., *Nature*, 2010, 468(7327):1067-1073).

Among ubiquitously expressed BET family proteins, BRD4 is unique in that it interacts with P-TEFb through its C-terminal tail (Bisgrove et al., *PNAS USA*, 2007, 104(34): 13690-95). Furthermore, BRD4 is a mammalian bromodomain protein that preferentially binds to acetylated histone H4 (H4-KAc) in living cells (Brasier et al., *J Virol*, 2011, 85(22):11752-69; Jang et al., *Mol Cell*, 2005, 19(4):523-34; Yang et al., *Nature*, 2001, 414(6861):317-22). Through H4-KAc binding, BRD4 is a critical mediator of transcriptional elongation, functioning to recruit activated CDK9 to the promoter (Jang et al., *Mol Cell*, 2005, 19(4):523-34; Yang et al., *Nature*, 2001, 414(6861):317-22).

Small inhibitors of BRD4 include, but are not limited to ZL0420, ZL0454, the compounds of Table 1, or a pharmaceutically acceptable salts thereof. Small molecules with similar characteristics would, in view of the current application, be useful in the methods described herein.

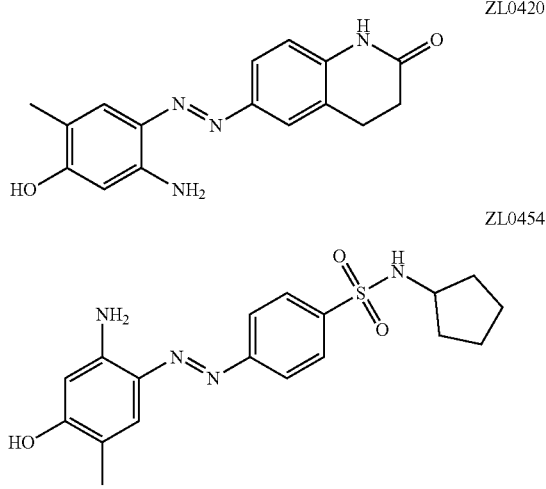

TABLE 1

List of representative compounds that have been synthesized and pharmacologically screened. Inhibitory effects of BRD4 inhibitors on induction of fibrotic genes including CIG5 and IL-6 in hSAECs.

| Compounds | Structure | CIG5 (%) | IL-6 (%) |
|---|---|---|---|
| ZL0420 | 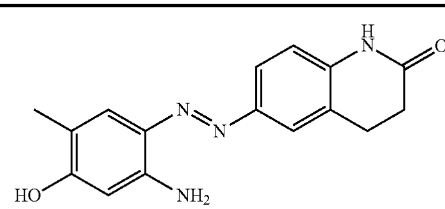 | 1.54 | 0.54 |
| ZL0454 | 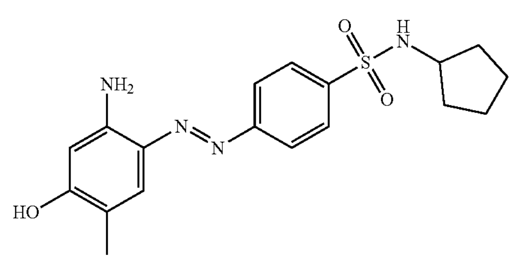 [SMILES: Cc1cc(/N=N/c2ccc(S(=O)(=O)NC3CCCC3)cc2)c(N)cc1O] | 15.6 | 0.9 |

TABLE 1-continued

List of representative compounds that have been synthesized and pharmacologically screened. Inhibitory effects of BRD4 inhibitors on induction of fibrotic genes including CIG5 and IL-6 in hSAECs.

| Compounds | Structure | CIG5 (%) | IL-6 (%) |
|---|---|---|---|
| ZL0556 | 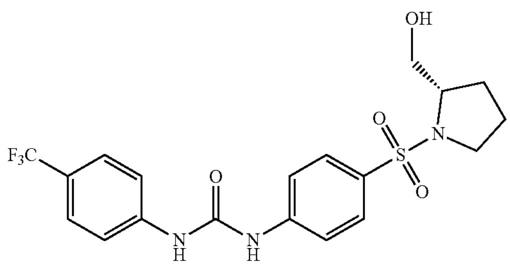 [SMILES: O=C(Nc1ccc(C(F)(F)F)cc1)Nc1ccc(S(=O)(=O)N2CCC[C@H]2CO)cc1] | 0.89 | 0.85 |
| ZL0586 | 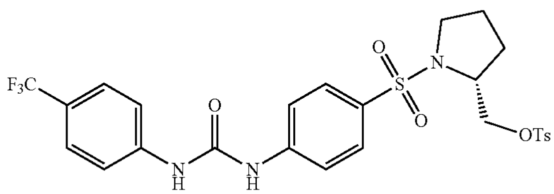 [SMILES: Cc1ccc(S(=O)(=O)OC[C@H]2CCCN2S(=O)(=O)c2ccc(NC(=O)Nc3ccc(C(F)(F)F)cc3)cc2)cc1] | 1.4 | 3.4 |
| ZL0590 | 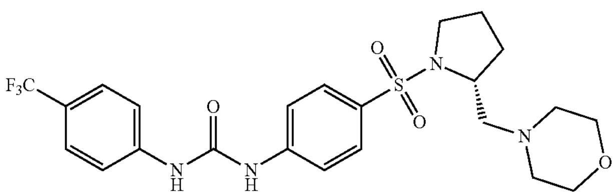 [SMILES: O=C(Nc1ccc(C(F)(F)F)cc1)Nc1ccc(S(=O)(=O)N2CCC[C@@H]2CN2CCOCC2)cc1] | 0.78 | 0.26 |
| ZL0591 | 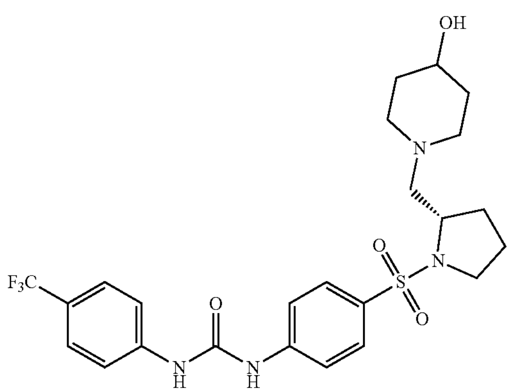 [SMILES: O=C(Nc1ccc(C(F)(F)F)cc1)Nc1ccc(S(=O)(=O)N2CCC[C@H]2CN2CCC(O)CC2)cc1] | 0.48 | 0.28 |
| ZL0589 | 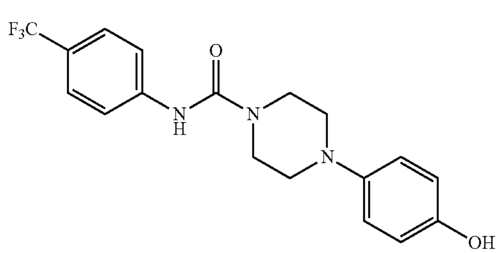 [SMILES: O=C(Nc1ccc(C(F)(F)F)cc1)N1CCN(c2ccc(O)cc2)CC1] | 5.6 | 4.2 |

TABLE 1-continued

List of representative compounds that have been synthesized and pharmacologically screened. Inhibitory effects of BRD4 inhibitors on induction of fibrotic genes including CIG5 and IL-6 in hSAECs.

| Compounds | Structure | CIG5 (%) | IL-6 (%) |
|---|---|---|---|
| ZL0468 | 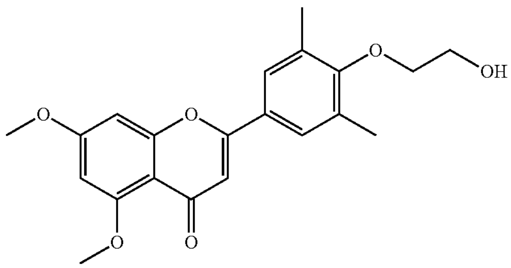 [SMILES: COc1cc(OC)c2c(=O)cc(-c3cc(C)c(OCCO)c(C)c3)oc2c1] | 3.14 | 2.25 |
| ZL0513 | 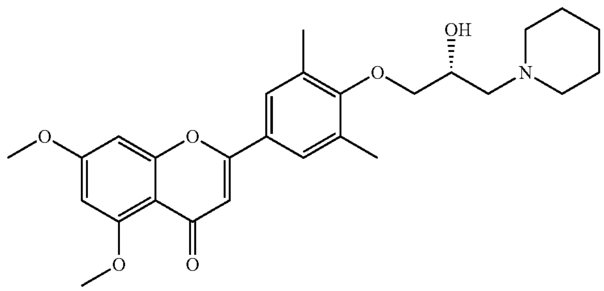 [SMILES: COc1cc(OC)c2c(=O)cc(-c3cc(C)c(OC[C@H](O)CN4CCCCC4)c(C)c3)oc2c1] | 0.81 | 0.3 |
| ZL0516 | 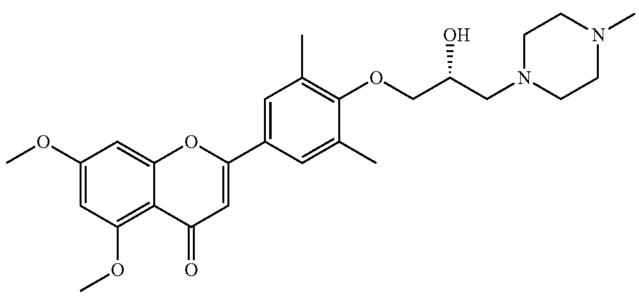 | 9.1 | 2.71 |
| ZL0165 | 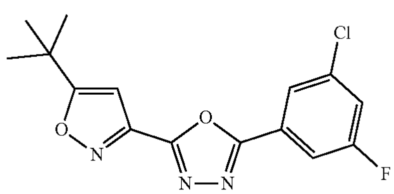 [SMILES: CC(C)(C)c1cc(-c2nnc(-c3cc(F)cc(Cl)c3)o2)no1] | 1.01 | 2.5 |

TABLE 2

Binding affinities of selected compounds with BRD4 BD1, BRD4 BD2, BRD2 BD1 and BRD2 BD2.

| Compounds | CIG5 ($IC_{50}$, µM) | IL-6 ($IC_{50}$, µM) | BRD4 ($IC_{50}$, µM) | | BRD2 ($IC_{50}$, µM) | |
|---|---|---|---|---|---|---|
| | | | BD1 | BD2 | BD1 | BD2 |
| JQ1 | 0.95 | 1.02 | 0.092 | 0.062 | 0.078 | 0.052 |
| RVX-208 | 1.66 | 3.29 | 1.142 | 0.135 | 5.78 | 0.251 |
| ZL0392 | 1.34 | 1.88 | 0.103 | 0.142 | | |
| ZL0420 | 0.42 | 0.45 | 0.027 | 0.032 | 0.803 | 1.736 |
| ZL0454 | 0.6 | 0.69 | 0.049 | 0.032 | 0.772 | 1.836 |
| HJC05100 | 3.5 | 3.2 | 0.183 | 0.147 | | |
| ZL0468 | 2.6 | 2.8 | 0.164 | 0.135 | | |

The term "pharmaceutically acceptable salts" as used herein, refers to salts of compounds of this invention that are substantially non-toxic to living organisms. Typical pharmaceutically acceptable salts include those salts prepared by reaction of a compound of this invention with an inorganic or organic acid, or an organic base, depending on the substituents present on the compounds of the invention.

Non-limiting examples of inorganic acids which may be used to prepare pharmaceutically acceptable salts include: hydrochloric acid, phosphoric acid, sulfuric acid, hydrobromic acid, hydroiodic acid, phosphorous acid and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydro fluoride, acetate, propionate, formate, oxalate, citrate, lactate, p-toluenesulfonate, methanesulfonate, maleate, and the like.

Suitable pharmaceutically acceptable salts may also be formed by reacting the agents of the invention with an organic base such as methylamine, ethylamine, ethanolamine, lysine, ornithine and the like. Pharmaceutically acceptable salts include the salts formed between carboxylate or sulfonate groups found on some of the compounds of this invention and inorganic cations, such as sodium, potassium, ammonium, or calcium, or such organic cations as isopropylammonium, trimethylammonium, tetramethylammonium, and imidazolium.

It should be recognized that the particular anion or cation forming a part of any salt of this invention is not critical, so long as the salt, as a whole, is pharmacologically acceptable.

Additional examples of pharmaceutically acceptable salts and their methods of preparation and use are presented in Handbook of Pharmaceutical Salts: Properties, Selection and Use (2002), which is incorporated herein by reference.

An "isomer" of a first compound is a separate compound in which each molecule contains the same constituent atoms as the first compound, but where the configuration of those atoms in three dimensions differs. Unless otherwise specified, the compounds described herein are meant to encompass their isomers as well. A "stereoisomer" is an isomer in which the same atoms are bonded to the same other atoms, but where the configuration of those atoms in three dimensions differs. "Enantiomers" are stereoisomers that are mirror images of each other, like left and right hands. "Diastereomers" are stereoisomers that are not enantiomers.

It is contemplated that any embodiment discussed in this specification can be implemented with respect to any method or composition of the invention, and vice versa. Furthermore, compositions of the invention can be used to achieve methods of the invention.

III. ANTI-INFLAMMATORY AGENTS

In certain aspects of the invention an anti-inflammatory agent may be used in combination with a composition described herein. The anti-inflammatory can be a steroidal or non-steroidal anti-inflammatory.

Steroidal anti-inflammatories for use herein include, but are not limited to fluticasone, beclomethasone, any pharmaceutically acceptable derivative thereof, and any combination thereof. As used herein, a pharmaceutically acceptable derivative includes any salt, ester, enol ether, enol ester, acid, base, solvate or hydrate thereof. Such derivatives may be prepared by those of skill in the art using known methods for such derivatization.

Fluticasone—Fluticasone propionate is a synthetic corticosteroid. Fluticasone propionate is a white to off-white powder and is practically insoluble in water, freely soluble in dimethyl sulfoxide and dimethylformamide, and slightly soluble in methanol and 95% ethanol. In an embodiment, the formulations of the present invention may comprise a steroidal anti-inflammatory (e.g., fluticasone propionate).

Beclomethasone—In certain aspects the steroidal anti-inflammatory can be beclomethasone dipropionate or its monohydrate. The compound may be a white powder and is very slightly soluble in water (Physicians' Desk Reference), very soluble in chloroform, and freely soluble in acetone and in alcohol.

Providing steroidal anti-inflammatories according to the present invention may enhance the compositions and methods of the invention by, for example, attenuating any unwanted inflammation. Examples of other steroidal anti-inflammatories for use herein include, but are not limited to, betamethasone, triamcinolone, dexamethasone, prednisone, mometasone, flunisolide and budesonide.

In accordance with yet another aspect of the invention, the non-steroidal anti-inflammatory agent may include aspirin, sodium salicylate, acetaminophen, phenacetin, ibuprofen, ketoprofen, indomethacin, flurbiprofen, diclofenac, naproxen, piroxicam, tebufelone, etodolac, nabumetone, tenidap, alcofenac, antipyrine, amimopyrine, dipyrone, ammopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, meclofenamic acid, mefenamic acid, niflumic acid, salidifamides, sulindac, suprofen, tolmetin, nabumetone, tiaramide, proquazone, bufexamac, flumizole, tinoridine, timegadine, dapsone, diflunisal, benorylate, fosfosal, fenclofenac, etodolac, fentiazac, tilomisole, carprofen, fenbufen, oxaprozin, tiaprofenic acid, pirprofen, feprazone, piroxicam, sudoxicam, isoxicam, celecoxib, Vioxx®, and/or tenoxicam.

IV. FORMULATION AND ADMINISTRATION

The pharmaceutical compositions disclosed herein may be administered, for example, via the respiratory system of a subject. In certain aspects the compositions are deposited in the lung by methods and devices known in the art. Therapeutic compositions described herein may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations contain a preservative to prevent the growth of microorganisms. In certain aspects the compounds described herein can be formulated for extended release as a nanoparticles (NPs) formulation, made from biodegradable and biocompatible polymers. Such therapeutic formulations offer a platform for reducing the number of doses, reduce toxicity without altering its therapeutic effects, protect the drug from inactivation (due to protein binding or metabolism of the drug), and provide a sustained release stable for long periods of time and have greater specificity against target tissues (given by the functionalization of the molecule).

The compositions described herein can be administered using conventional modes of delivery including, but not limited to, intravenous, intraperitoneal, oral, intralymphatic, subcutaneous administration, intraarterial, intramuscular, intrapleural, intrathecal, and by perfusion through a regional catheter. When administering the compositions by injection, the administration may be by continuous infusion or by single or multiple boluses. For parenteral administration, the therapeutic agents may be administered in a pyrogen-free, parenterally acceptable aqueous solution comprising the desired therapeutic agents in a pharmaceutically acceptable vehicle. A particularly suitable vehicle for parenteral injection is sterile distilled water in which an one or more therapeutic agents are formulated as a sterile, isotonic solution, properly preserved.

Doses of compounds being administered, alone or as part of a pharmaceutical composition, are between about 0.001 mg/kg and 1 mg/kg body weight, preferably between about 1 and 100 μg/kg body weight, most preferably between 1 and 10 μg/kg body weight. Therapeutic compositions may be administered 1, 2, 3, 4, 5, 6, 7, 8, 9, 10, 11, 12, 13, 14, 15, 16, 17, 18, 19, 20 or more times, and they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months.

Therapeutically effective doses will be easily determined by one of skill in the art and will depend on the severity and course of the disease, the patient's health and response to treatment, the patient's age, weight, height, sex, previous medical history and the judgment of the treating physician.

The pharmaceutical forms suitable for inhalation include sterile aqueous solutions or dispersions and sterile powders for the extemporaneous preparation of sterile inhalable solutions or dispersions. In all cases the form is typically sterile and capable of inhalation directly or through some intermediary process or device. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. The prevention of the action of microorganisms can be brought about by various antibacterial and antifungal agents, for example, parabens, chlorobutanol, phenol, sorbic acid, thimerosal, and the like.

Some variation in dosage will necessarily occur depending on the condition of the subject being treated and the particular circumstances involving exposure or potential exposure. The person responsible for administration will, in any event, determine the appropriate dose for the individual subject. Moreover, for human administration, preparations should meet sterility, pyrogenicity, general safety, and purity standards as required by FDA Office of Biologics standards or other similar organizations.

Sterile compositions are prepared by incorporating the active components in the required amount in the appropriate solvent with various other ingredients enumerated above, as required, followed by, for example, filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile compositions, some methods of preparation are vacuum-drying and freeze-drying techniques which yield a powder of the component(s) and/or active ingredient(s) plus any additional desired ingredient from a previously sterile-filtered solution.

In certain embodiments the compounds can be associated with the surface of, directly or indirectly conjugated to, encapsulated within, surrounded by, dissolved in, or dispersed throughout a polymeric matrix. The phrase "loaded into", "loaded onto", "incorporated into", or "included in" are used interchangeably to generally describe the association of the compound with the particle without imparting any further meaning as to where or how the compound is associated with the particle.

The amount of compound present in a particle (entrapment efficiency) can be at least about 10% to as high as about 98% w/w. In some embodiments, the entrapment efficiency can be about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 98% (w/w).

A. Nanoparticles

The composition (e.g., encapsulated compound) comprises a nanoparticle, the nanoparticle further comprising a polymer and at least one compound. The term "particle," "nanoparticle," "biodegradable polymeric nanoparticle," or the abbreviation "NP" for nanoparticle, as used herein, can refer to particles between 10, 100, 200, 300, 400, 500, to 600, 700, 800, 900, 1000 nanometers (nm) in diameter, including all values and ranges there between, and are used interchangeably. In certain aspects the NPs can have a diameter of 50 to 150 nm. The compounds described herein can be incorporated into a suitable particle (or nanoparticle) to aid in the delivery of the drug to target cells, to increase the stability of the composition, to minimize potential toxicity of the composition, and/or a combination thereof. A variety of nanoparticles are suitable for delivering a compound.

The size of the particle can influence the ability of the particle to rapidly penetrate through mucosal barriers. For instance, the nanoparticle can have small particle size for successful delivery through a mucosal barrier. In some embodiments, the diameter of a nanoparticle can be at least 10 nm, at least 20 nm, at least 30 nm, at least 40 nm, at least 50, at least 60 nm, at least 70 nm, at least 80 nm, at least 90 nm, or at least 100 nm. In other embodiments, the particle can be greater than about 100 nm in diameter. For example, the diameter of the nanoparticle can be at least 110 nm, at least 120 nm, at least 130 nm, at least 140 nm, at least 150 nm, at least 160 nm at least 170 nm, at least 180 nm, at least 190 nm, or at least 200 nm. In an exemplary embodiment, the nanoparticle can be less than 220 nm in diameter. In still other embodiments, the particle can be about or less than about 100 nm in diameter.

In some embodiments, the particle can have a surface charge that is positive or negative. For example, in certain embodiments where a nanoparticle has a negative surface charge, the surface charge can be at least −40 millivolts (mV), at least −35 mV, at least −30 mV, at least −25 mV, at least −20 mV, no greater than −10 mV, no greater than −15 mV, no greater than −20 mV, no greater than −25 mV, or any combination thereof. In one example, a nanoparticle can have a negative surface charge of at least −30 mV to no greater than −10 mV. In other examples a nanoparticle has a positive surface charge, the surface charge can be at least 2 millivolts (mV), at least 15 mV, at least 20 mV, at least 25 mV, or at least 30 mV, no greater than 40 mV, no greater than 35 mV, no greater than 30 mV, no greater than 25 mV, or any combination thereof.

In some embodiments, the particle can have an osmolarity of less than about 1000 mOsm/kg. In other embodiments, the particle can have an osmolarity less than about 500 mOsm/kg. For example, the particle can have an osmolarity of about 50 mOsm/kg, about 100 mOsm/kg, about 150 mOsm/kg, about 200 mOsm/kg, about 250 mOsm/kg, about 300 mOsm/kg, about 350 mOsm/kg, about 400 mOsm/kg, about 410 mOsm/kg, about 420 mOsm/kg, about 430 mOsm/kg, about 440 mOsm/kg, about 450 mOsm/kg, about 460 mOsm/kg, about 470 mOsm/kg, about 480 mOsm/kg, or about 490 mOsm/kg. In another embodiment, the particle can have an osmolarity of at least 500 mOsm/kg to no greater than 1000 mOsm/kg. For example, the particle can have an osmolarity of about 500 mOsm/kg, about 600 mOsm/kg, about 700 mOsm/kg, about 800 mOsm/kg, about 900 mOsm/kg, or about 1000 mOsm/kg.

B. Biodegradable Polymer

Each particle can include one or more biodegradable polymers. An example of such a particle comprising a biodegradable polymer and methods of making the particle is disclosed in patent application publication number US 2011/0236437, which is incorporated herein by reference in its entirety. Briefly, a "polymer" as used herein, is given its ordinary meaning as used in the art, i.e., a molecular structure including one or more repeat units (monomers), connected by covalent bonds. The repeat units can all be identical, or in some cases, there can be more than one type of repeat unit present within the polymer. A polymer can be natural (e.g., biologically derived) or unnatural (e.g., synthetically derived). Polymers can be homopolymers or copolymers including two or more monomers. Copolymers can be random, block, or can include a combination of random and block sequences. If more than one type of repeat unit is present within the polymer, then the polymer is said to be a "copolymer". It is to be understood that in any aspect employing a polymer, the polymer can be a copolymer.

A biodegradable polymer is able to degrade, chemically and/or biologically, within a physiological environment, such as within the body. For instance, the polymer can be one that hydrolyzes spontaneously upon exposure to water (e.g., within a subject), or degrades upon exposure to heat (e.g., at temperatures of 42° C.). Degradation of a polymer can occur at varying rates, depending on the polymer or copolymer used. For example, the half-life of the polymer (the time at which 50% of the polymer is degraded into monomers and/or other nonpolymeric moieties) can be on the order of days or weeks, depending on the polymer. The polymers can be biologically degraded, e.g., by enzymatic activity or cellular machinery. In some cases, the polymers can be broken down into monomers and/or other nonpolymeric moieties that cells can either reuse or dispose of without significant toxic effect on the cells (for example, polylactide can be hydrolyzed to form lactic acid, polyglycolide can be hydrolyzed to form glycolic acid, etc.).

In some embodiments, the biodegradable polymer can be a natural polymer. In other embodiments, biodegradable the polymer can be a synthetic polymer. Non-limited examples of natural and synthetic polymers useful in the preparation of biodegradable particles can include carbohydrates such as alginate, cellulose, polyhydroxyalkanoates, polyamides, polyphosphazenes, polypropylfumarates, polyethers, polyacetals, polycyanoacrylates, biodegradable polyurethanes, polycarbonates, polyanhydrides, polyhydroxyacids. poly(ortho esters), and polyesters. Non-limiting examples of poly-esters can include polymers including, but not limited to, polycaprolactone, or copolymers including, but not limited to, lactic acid and glycolic acid units, such as poly(lactic acid-coglycolic acid) and poly(lactide-co-glycolide), collectively referred to herein as "PLGA"; and homopolymers including glycolic acid units, and lactic acid units, such as poly-L-lactic acid, poly-D-lactic acid, poly-D,L-lactic acid, poly-L-lactide, poly-D-lactide, and poly-D,L-lactide. In some embodiments, the polymer can be PLGA.

Pulmonary/respiratory drug delivery can be implemented by different approaches, including liquid nebulizers, aerosol-based metered dose inhalers (MDI's), sprayers, dry powder dispersion devices and the like. Such methods and compositions are well known to those of skill in the art, as indicated by U.S. Pat. Nos. 6,797,258; 6,794,357; 6,737,045; and 6,488,953—all of which are incorporated by reference. According to the invention, at least one pharmaceutical composition can be delivered by any of a variety of inhalation or nasal devices known in the art for administration of a therapeutic agent by inhalation. Other devices suitable for directing pulmonary or nasal administration are also known in the art. Typically, for pulmonary administration, at least one pharmaceutical composition is delivered in a particle size effective for reaching the lower airways of the lung or sinuses. Some specific examples of commercially available inhalation devices suitable for the practice of this invention are Turbohaler™ (Astra), Rotahaler®) (Glaxo), Diskus® (Glaxo), Spiros™ inhaler (Dura), devices marketed by Inhale Therapeutics, AERx™ (Aradigm), the Ultravent® nebulizer (Mallinckrodt), the Acorn II® nebulizer (Marquest Medical Products), the Ventolin® metered dose inhaler (Glaxo), the Spinhaler® powder inhaler (Fisons), Aerotech II® or the like.

All such inhalation devices can be used for the administration of a pharmaceutical composition in an aerosol. Such aerosols may comprise either solutions (both aqueous and non-aqueous) or solid particles. Metered dose inhalers typically use a propellant gas and require actuation during inspiration. See, e.g., WO 98/35888 and WO 94/16970. Dry powder inhalers use breath-actuation of a mixed powder. See U.S. Pat. Nos. 5,458,135 and 4,668,218; PCT publications WO 97/25086, WO 94/08552 and WO 94/06498; and European application EP 0237507, each of which is incorporated herein by reference in their entirety. Nebulizers produce aerosols from solutions, while metered dose inhalers, dry powder inhalers, and the like generate small particle aerosols. Suitable formulations for administration include, but are not limited to nasal spray or nasal drops, and may include aqueous or oily solutions of a composition described herein.

A spray comprising a pharmaceutical composition described herein can be produced by forcing a suspension or solution of a composition through a nozzle under pressure. The nozzle size and configuration, the applied pressure, and the liquid feed rate can be chosen to achieve the desired output and particle size. An electrospray can be produced, for example, by an electric field in connection with a capillary or nozzle feed.

A pharmaceutical composition described herein can be administered by a nebulizer such as a jet nebulizer or an ultrasonic nebulizer. Typically, in a jet nebulizer, a compressed air source is used to create a high-velocity air jet through an orifice. As the gas expands beyond the nozzle, a low-pressure region is created, which draws a composition through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer.

In an ultrasonic nebulizer, high-frequency electrical energy is used to create vibrational, mechanical energy, typically employing a piezoelectric transducer. This energy is transmitted to the composition creating an aerosol.

In a metered dose inhaler (MDI) or in other device that us propellant, a propellant, a composition, and any excipients or other additives are contained in a canister as a mixture with a compressed gas. Actuation of the metering valve releases the mixture as an aerosol. Pharmaceutical compositions for use with a metered-dose inhaler device will generally include a finely divided powder containing a composition of the invention as a suspension in a non-aqueous medium, for example, suspended in a propellant with the aid of a surfactant. The propellant can be any conventional material employed for this purpose such as chlorofluorocarbon, a hydrochlorofluorocarbon, a hydrofluorocarbon, or a hydrocarbon including trichlorofluoromethane, dichlorodifluoromethane, dichlorotetrafluoroethanol and 1,1,1,2-tetrafluoroethane, HFA-134a (hydrofluroalkane-134a), HFA-227 (hydrofluroalkane-227), or the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a subject. The preparation of an aqueous composition that contains a polypeptide or peptide as an active ingredient is well understood in the art.

V. EXAMPLES

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Enhanced mesenchymal signatures are observed in bronchial biopsies from patients with allergic asthma. The inventors sought to elucidate the molecular mechanisms using cat dander, a prevalent aeroallergen associated with asthma risk.

Repetitive exposure to cat dander induces fibrogenic, mesenchymal transition (EMT) and disrupts E cadherin expression in primary human small airway epithelial cells. In a murine model of repetitive cat dander exposure, we observe that the IκB kinase (IKK)-NFκB signaling pathway is required for mucosal EMT, airway remodeling and expansion of the myofibroblast population. Cat dander exposure induces NFκB/RelA to complex with—and activate the chromatin reader, bromodomain-containing protein 4 (BRD4), to become an epigenetic regulator responsible for activating RNA Pol II and remodeling of inflammatory and fibrogenic genes through its atypical histone acetyltransferase (HAT) activity. The inventors demonstrate that a novel, small-molecule BRD4 inhibitor (ZL0454) disrupts BRD4 binding to the NFκB-RNA Pol II complex and inhibits its HAT activity. BRD4 inhibitors prevent EMT, myofibroblast expansion, IgE sensitization, and fibrosis in airways of naïve mice exposed to cat dander.

NFκB-inducible BRD4 activity is an epigenetic regulator of aeroallergen sensitization and airway remodeling. Therapeutic modulation of this pathway affects allergen-induced epithelial cell state changes, ECM production and expansion of the subepithelial myofibroblast population.

A. Materials and Methods

Repetitive CDE (rCDE) Challenges.

12 week old male wild-type (WT) C57BL/6 mice were purchased from Jackson Laboratory (Bar Harbor, Me.). CDE (Stallergenes/Greer laboratories, 20 µg/dose) was administered to naïve C57BL6/J mice every other day via the intranasal route for a total of 15 administrations (n=5 mice/group). In the IKK inhibitor experiments, mice were either pretreated with vehicle or the selective IKK inhibitor [BMS345541, 10 mg/kg via the intraperitoneal (ip) route]. In the BRD4 inhibitor experiments, mice were either pretreated with vehicle or the selective BRD4 inhibitor (ZL0454, 10 mg/kg via ip). Mice were sacrificed 12 d later to allow resolution of the acute inflammation.

Histological Assessment of Inflammation and Fibrosis.

Formalin-fixed lungs were embedded in paraffin, sectioned at a 4 µm thickness, and stained with hematoxylin and eosin or Masson's trichrome. Microscopy was performed on a NIKON Eclipse Ti System 16, 17. Pulmonary fibrosis was graded using a modified Ashcroft scoring method 16, 17. In brief, to determine the fibrosis histopathology score for the lung of each mouse, the entire left and right longitudinal lung sections were scored separately (score range, 0 to 9) at ×100 magnification, and the scores were combined (total score range, 0 to 18)[16, 17].

Statistical Analysis.

One-way ANOVA was performed when looking for time differences followed by Tukey's post-hoc test to determine significance. $P<0.05$ was considered significant.

Human Subjects.

Human subjects were enrolled after providing informed consent to a protocol approved by the University of Texas Medical Branch Galveston (UTMB) IRB. Demographic information was obtained to include duration of asthma, age at diagnosis, current medications, and history of exacerbations, in a manner consistent with previous US SARP or US ACRN2 study protocols[32, 33]. Bronchial mucosal biopsies were obtained from the right middle and right lower lobes, and were stored in RNA Later®. Extracted total RNA from mucosal biopsy samples was analyzed for mRNA expressions of EMT genes using Q-RT-PCR.

Cell Culture and Treatment.

Immortalized human small airway epithelial cells (hSAECs) were previously described[25]. hSAECs were grown in SAGM small airway epithelial cell growth medium (Lonza, Walkersville, Md.) in a humidified atmosphere of 5% $CO_2$. BMS345541 was purchased from Sigma Aldrich. CDE was purchased from Greer Laboratories. The BRD4 selective small molecule inhibitor ZL0454 [(E)-4-((2-Amino-4-hydroxy-5-methylphenyl)diazenyl)-N-cyclopentylbenzenesulfonamide] was synthesized and characterized by instrumental analyses including NMR, mass spectrometry and, HPLC as previously described[74]. ZL0454 was used at 10 µM concentrations in cell culture medium and 10 mg/kg body weight in vivo.

hSAECs expressing a doxycycline (Dox)-regulated shRNA were produced by lentiviral transduction. TRIPZ Tet-on inducible lentiviral RelA shRNA and TRIPZ Inducible lentiviral empty vector shRNAs plasmids were commercially obtained (Dharmacon, GE Life Sciences, Lafayette, Colo.) and packaged after transfection of BOS23 cells. hSAECs were infected with collected virus-containing supernatants and selected for puromycin resistance (4 µg/ml). Puromycin resistant hSAECs were pooled and characterized. RelA depletion was produced by addition of doxycycline to the culture medium (2 µg/ml, 5 d).

Animal Studies.

Animal experiments were performed according to the NIH Guide for Care and Use of Experimental Animals and approved by the University of Texas Medical Branch (UTMB) Animal Care and Use Committee (approval no. 1312058A). Mice were housed under pathogen-free conditions with food and water ad libitum.

Bronchoalveolar lavage and tissue processing. Animals were anesthetized, bronchoalveolar lavage fluid (BALF) was obtained and the mice sacrificed. Lung tissues were taken for total RNA extraction or fixed for histological examination. For histological examination, lungs were inflated under 25 cm $H_2O$ pressure with 10% (v/v) neutral buffered formalin through the tracheal cannula and immersed in 10% buffered formalin for at least 24 h. After being processed into paraffin blocks, the lungs were cut into 5-μm sections and stained with Masson Trichrome to assess fibrotic changes. Microscopy was performed on a NIKON Eclipse Ti System[75].

Periodic acid-Schiff (PAS) staining (pink color) was performed in parallel to demonstrate mucin secretion in airway epithelium[76, 77]. Quantification of accumulated mucin was assessed by 2 investigators who were blind to the treatment groups on a subjective scale of 0, 1, 2, 3, and 4 corresponding to none, mild, moderate, marked, or severe mucin deposition, respectively. Data were expressed as means of scores recorded by 2 blinded investigators[76,77].

BALF Analysis of Cellular Inflammation.

Cellular recruitment into the airway lumen was assessed in the collected bronchoalveolar lavage fluid (BALF) of mice. Lungs were perfused twice with 1 mL of sterile PBS (pH 7.4) and total cell counts determined by trypan blue staining and counting using a hemocytometer. Differential cell counts were performed on cytocentrifuge preparations (Cytospin 3; Thermo Shandon, Pittsburgh, Pa.) stained with Wright-Giemsa. A total of 300 cells were counted per sample using light microscopy.

Quantitative Real-Time PCR (Q-RT-PCR).

For gene expression analyses, 0.1 μg of cDNA product from reverse transcription of total RNA was amplified using SYBR Green Supermix (Bio-Rad) and gene-specific primers as previously described[75, 78]. Quantification of relative changes in gene expression was calculated using the ΔΔCt method[79,80] and expression as the fold change between experimental and control samples was normalized to internal control peptidylprolyl isomerase A (PPI1A)/cyclophilin A.

Confocal Immunofluorescence Microscopy.

hSAECs were incubated ±CDE (20 μg/mL) for 15 d, re-plated on glass cover slips pretreated with rat tail collagen (Roche Applied Sciences), and fixed with 4% paraformaldehyde in PBS. Afterwards, the fixed cells were stained with Alexa Fluor® 488- or 568-phalloidin (Life Technologies) for cytoplasmic distribution of F-actin (green or red color) and also counterstained with 4',6-diamidino-2-phenylindole (DAPI) for nuclear staining (blue color). The cells were visualized with a Nikon fluorescence confocal microscope at a magnification of 63×[75, 78].

For immunofluorescence staining, hSAECs were plated on rat tail collagen-treated cover glasses and stimulated with CDE for the indicated times. The cells were fixed with 4% paraformaldehyde in PBS and incubated with 0.1 m ammonium chloride for 10 min. Cells were permeabilized with 0.5% Triton-100, followed by incubation in blocking buffer (5% goat serum, 0.1% IGEPAL CA-630, 0.05% NaN3, and 1% BSA) and incubated with primary antibodies of RelA (Santa Cruz. 1:300 dilution), VIM, SNAIL CDH1, p267 RelA, H3K122ac, and pPol II Ser2 (Abcam, 1:200 dilution) in incubation buffer (0.1% IGEPAL CA-630, 0.05% NaN3, and 2% BSA) overnight at 4° C. After washing, cells were stained with Alexa Fluor 488- or 568-conjugated goat anti-rabbit IgG (Life Technologies) respectively in incubation buffer for 1 h, then visualized with a LSM510 fluorescence confocal microscope, magnification 63×.

Confocal Immunofluorescence assays of lung sections were performed on formalin-fixed, paraffin-embedded sections after rehydration using serial concentrations of ethanol. Antigen retrieval was performed in Tris-EDTA buffer (pH 9.0). Lung sections were blocked using 0.1% Triton-X, 5% normal goat serum in phosphate buffered saline (PBS) and incubated with primary antibodies of rabbit anti-p276RelA, pIKKα/β, SNAIL H3K122ac, COL1A, VIM, FN1, and αSMA (Abcam, 1:100 dilution) overnight at 4° C. Normal anti-rabbit IgG were used as staining specificity controls. After washing, lung sections were stained with Alexa Fluor 488- or 568-conjugated goat anti-rabbit IgG (Life Technologies) in incubation buffer for 1 h. Nuclei were stained with 4', 6-diamidino-2-phenylindole (DAPI) (5 μg/ml in PBS, 20 min) and mounted slides visualized with a LSM510 fluorescence confocal microscope, magnification 63×.

IgE Measurement.

Total IgE in serum were measured using Sandwich ELISA. 96-well plates 4 HBX (Thermo Scientific, Hudson, N.H., USA) were coated with the purified rat anti-mouse IgE capture antibody (BD Biosciences, San Jose, Calif., USA) for 2 hours at room temperature. After three washing, the plates were blocked with Sea Block blocking buffer (Pierce Biotechnology, Inc, Rockford, Ill., USA). Serum were added and incubated overnight. After washing, the plates were incubated with biotin-conjugated rat IgE (BD Biosciences, San Jose, Calif., USA) for 2 hours at room temperature, then washed and incubated with avidin-conjugated alkaline phosphatase for 45 minutes at 4° C. After washing, fluorometric values for each well were measured after addition of Atto-Phos substrate solution (Promega, Madison, Wis., USA)[76, 77].

Cat dander-specific IgE measurement was performed on 96-well plates. Plates were coated with 100 μg/ml of cat dander protein overnight at room temperature and blocked for 2 hour with sea block buffer. Plates were applied with serum overnight. After washing, the plates were incubated with biotin-conjugated rat IgE (BD Biosciences, San Jose, Calif., USA) for another 2 hours at room temperature, then washed and incubated with avidin-conjugated alkaline phosphatase for 45 minutes at 4° C. After washing, fluorometric values for each well were measured after addition of Atto-Phos substrate.

Analysis of Collagen Content.

To estimate amount of collagen in the lung tissue and BALF, hydroxyproline content was measured colorimetrically using a hydroxyproline assay kit (Sigma-Aldrich, St. Louis, Mo.) with minor modifications[24, 25]. Briefly, the lungs were weighed, homogenized in liquid nitrogen with 2 ml PBS, after which 2.0 ml of 12 N HCl was added, and the samples were hydrolyzed at 120° C. within a PTFE-lined capped pressure-tight vial for 6 h. Separately, 100 μl of BALF was hydrolyzed with 12 N HCl as above. Afterwards, 10 μl hydrolyzed samples were mixed with 100 μl of chloramine T/oxidation buffer at room temperature for 5 min and later incubated with the 4-(Dimethylamino) benzaldehyde (DMAB) reagent for 90 min at 60° C. The absorbance of oxidized hydroxyproline was determined by absorbance 560 nm (Infinite M200 PRO multimode microplate reader, Tecan Instruments). Standard curves were generated for each assay using hydroxyproline standards. The amount of collagen was expressed in micrograms per milligram lung tissue while it was expressed in nanograms per milliliters in BALF. The data shown are the means±S.D. from n=5 experiments.

In Situ Proximity Ligation Assay (PLA).

Paraffin embedded lung section slides were subjected to antigen retrieval, permeabilized with 0.1% Triton X-100, and incubated with IgG or primary rabbit Ab to RelA (Santa Cruz), and mAb to BRD4 (Sigma Aldrich). Slides were then subjected to PLA using the Duolink PLA kit from OLink Bioscience (Uppsala, Sweden) according to the manufacturer's instructions. The nuclei were counterstained with DAPI, and the PLA signals were visualized in a LSM510 fluorescence confocal microscope at 63× Magnification.

B. Results

Activation of the EMT Gene Program in Human Asthmatic Mucosa.

Figure 1:
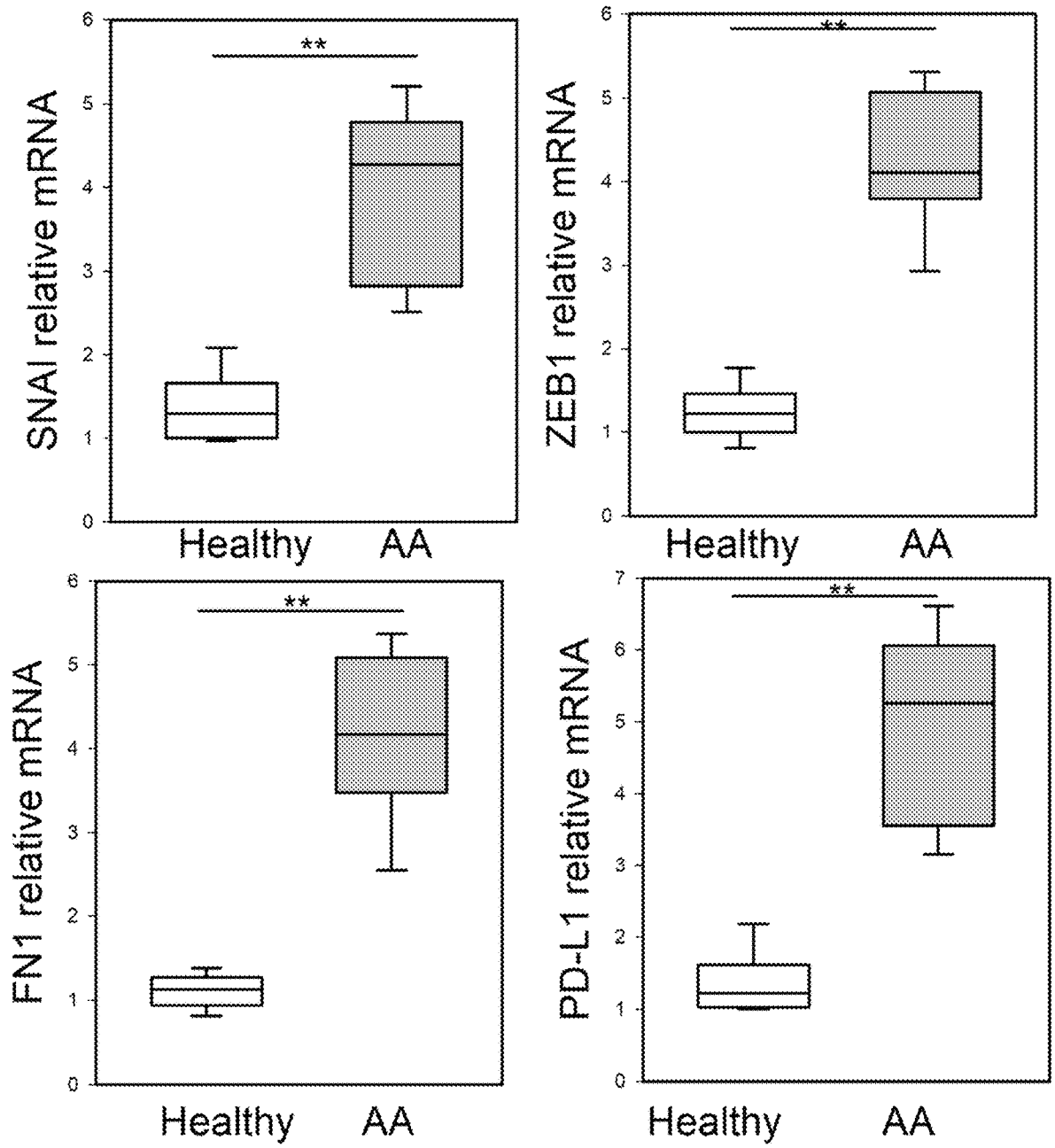
FIG. 1. EMT signature in mucosal samples in patients with severe asthma. qRT-PCR for bronchial mucosal biopsy specimens from healthy subjects or patients with mild-to-moderate asthma for the EMT regulators SNAI1, ZEB1, and FN1 or the myofibroblast activation marker PD-L1 mRNA expression. Results are shown as fold change mRNA abundance normalized to PPIA (cyclophilin A). **$P<0.01$ compared with healthy human samples (n=5 healthy subjects and 7 patients with atopic asthma [AA]), t test.

Although epithelial stress response and damage are characteristic findings in human asthma 20, the role of EMT in allergic disease is not known[21-23]. Mucosal biopsies from normal and with mild-moderate asthmatics with positive allergen skin tests were obtained (See Table 3). Relative to controls, the inventors observed a significant 3.1-fold increase in the EMT core regulators SNAI1 mRNA and a similar upregulation of ZEB1 mRNA in allergic asthmatics (FIG. 1). In addition, a 3.6-fold increase in the ECM gene, fibronectin (FN1), and myofibroblast activation marker, CD274/Programmed Death Ligand (PD-L1) was observed (FIG. 1). Collectively, these data suggest the activation of the mesenchymal remodeling program in mucosa of allergic asthmatics.

Tonic CDE Exposure Induces Epithelial Mesenchymal Transition.

Figure 9:
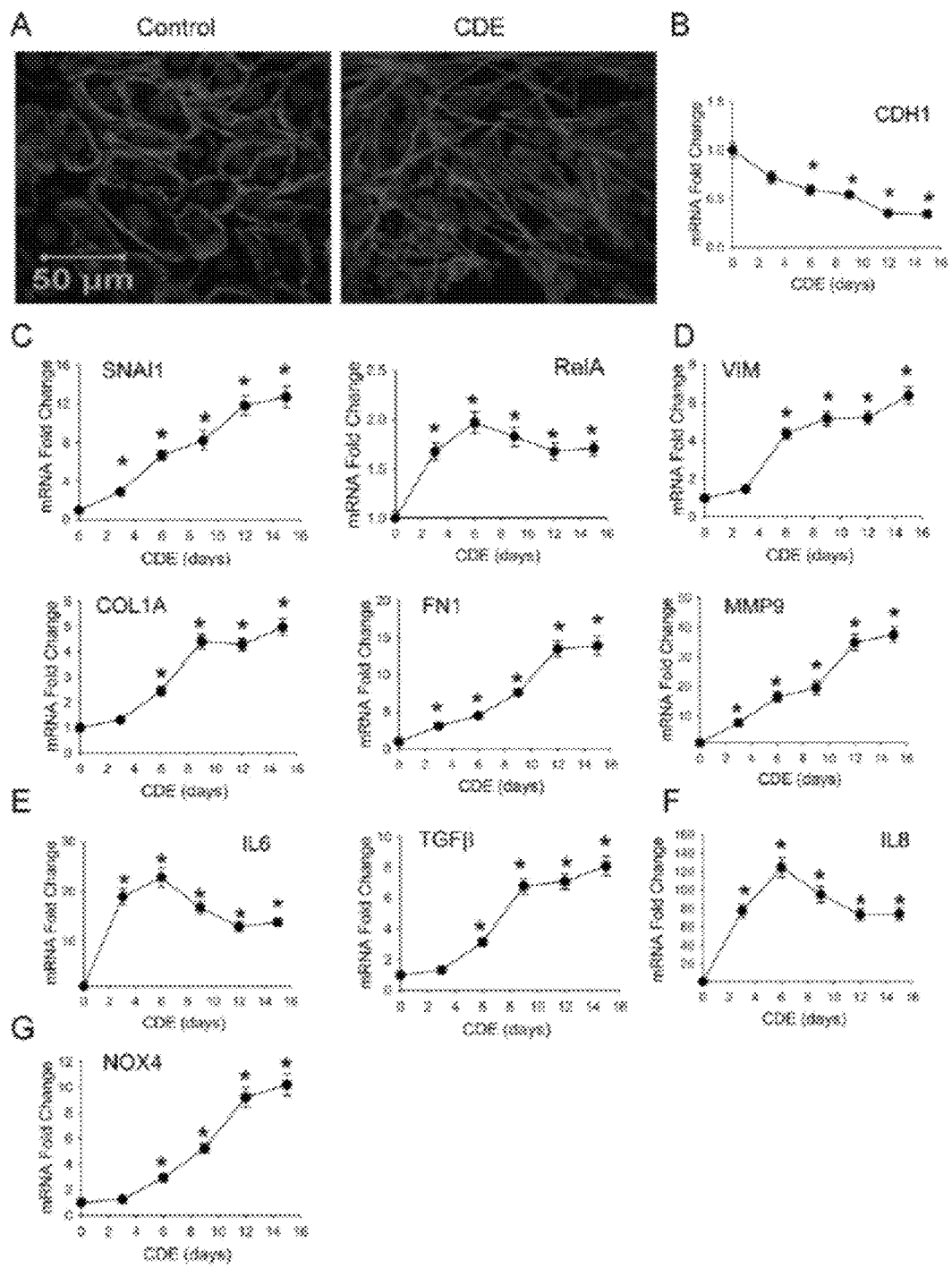
FIG. 9. Chronic CDE stimulation induces mesenchymal transition of airway epithelial cells. A, Confocal immunofluorescence micrographs of human small airway epithelial cells (hSAECs) incubated in the absence or presence of CDE (20 μg/mL) for 15 days. Cells were stained with Alexa568-conjugated phalloidin (red color) and DAPI (a nuclear DNA stain, blue color). Graphs are shown at 63× magnification. B, Q-RT-PCR assays of total RNA extracted from a time course of CDE-stimulated hSAECs for the epithelial marker CDH1 (E-cadherin). Shown as fold-change mRNA abundance normalized to PPIA (cyclophilin A). * $p<0.01$, n=3. C, Q-RT-PCR of SNAI1 and RelA mRNAs. D, Q-RT-PCR for vimentin (VIM), collagen 1A (COL1A), fibronectin (FN1), and MMP9. E, Q-RT-PCR for paracrine growth factor expression. of IL6 and TGFβ mRNA. F, Q-RT-PCR for CXCL1/IL8. G, Q-RT-PCR for inducible NADPH oxidase, NOX4. All Q-RT-PCR data are the means±S.D. from n=3 experiments.

Because cat dander exposures are chronic, the inventors initially studied the effect of tonic CDE on model human small airway epithelial cells (Tert-hSAECs). Tert-hSAECs express differentiated cytokeratin isoforms[24] and exhibit overlapping genomic and proteomic signatures with those of primary terminally differentiated cells, yet do not exhibit artefactual senescence[24-26]. Knowing that CDE activates NFκB6, a transcription factor that mediates TGFβ-induced cell-state changes[15, 16], the inventors examined the effect of tonic CDE stimulation on hSAEC mesenchymal transition. Tonic CDE stimulation induced hSAECs to assume an elongated shape with enhanced formation of filamentous (F) actin throughout the cytoplasm and nucleus (see FIG. 9A), suggesting acquisition of front-rear polarity and mesenchymal transition[15, 16].

The EMT program involves silencing epithelial markers and activating mesenchymal genes mediated by the core mesenchymal transcription factors, SNAI1 and RelA[15, 23, 27]. The inventors observed that tonic CDE exposure induced RelA and SNAI1 expression with SNAI1 monotonically increasing to an apparent plateau of 12-fold (see FIG. 9B). Additionally, mRNA expression of the mesenchymal intermediate protein, vimentin (VIM) and the ECM remodeling proteins FN1, collagen (COL1A), and matrix metalloproteinase 9 (MMP9) (see FIG. 9C). Tonic CDE induced expression of IL6 and TGFβ mesenchymal growth factors. The inventors also observed inducible NOX4 mRNA, an NADPH oxidase responsible for ROS stress and DNA damage response[28-30].

TABLE 3

Clinical demographics of human subjects.

| Dx/Study ID | Skin Test | FEV1% | FVC % | FEV1:FVC |
|---|---|---|---|---|
| Control-102 | Negative | 91 | 87 | 0.88 |
| Control-103 | Negative | 114 | 113 | 0.84 |
| Control-104 | Negative | 79 | 78 | 0.82 |
| Control-107 | Negative | 88 | 86 | 0.82 |
| MMA -80 | Positive-Dust mite | 99 | 106 | 0.78 |
| MMA -82 | Positive-*Penicillium* | 98 | 109 | 0.77 |
| MMA -83 | Positive-*Penicilliium, Alternaria* | 94 | 107 | 0.72 |

| Subject ID | Age (y) | Sex | Treatment | Disease status | $FEV_1$ (% predicted) | FVC (% predicted) |
|---|---|---|---|---|---|---|
| 1 | 33 | M | None | Normal | 4.72 | 5.70 |
| 2 | 28 | F | None | Normal | 3.37 | 3.75 |
| 3 | 30 | M | None | Normal | 3.67 | 4.61 |
| 4 | 31 | M | None | Normal | 4.07 | 4.95 |
| 5 | 26 | F | None | Normal | 6.67 | 4.20 |
| | | | | Average | 3.9 | 4.642 |
| 6 | 56 | F | ICS, SABA | Mild-moderate asthma | 2.52 | 3.05 |
| 7 | 28 | M | ICS, SABA | Mild-moderate asthma | 2.71 | 4.30 |
| 8 | 55 | F | ICS, SABA | Mild-moderate asthma | 2.07 | 2.76 |
| 9 | 29 | M | SABA, LABA, ICS | Mild-moderate asthma | 4.31 | 6.95 |
| 10 | 56 | F | ICS, SABA | Mild-moderate asthma | 2.16 | 2.87 |
| 11 | 46 | F | LABA | Severe asthma | 2.53 | 3.02 |
| 12 | 51 | F | ICS, SABA | Severe asthma | 0.78 | 1.74 |
| | | | | Average | 2.44 | 3.53 |

MMA, mild-moderate asthma; FEV1, forced expiratory volume in 1 sec; FVC, forced vital capacity; %, percent predicted.
F, Female;
FVC, forced vital capacity;
ICS, inhaled corticosteroid;
LABA, long-acting $\beta_2$-agonist;
M, male,
SABA, short-acting $\beta_2$-agonist NF κB/RelA is Required for CDE-Induced Mesenchymal Reprogramming of Airway EPITHELIAL CELLS.

Figure 2:
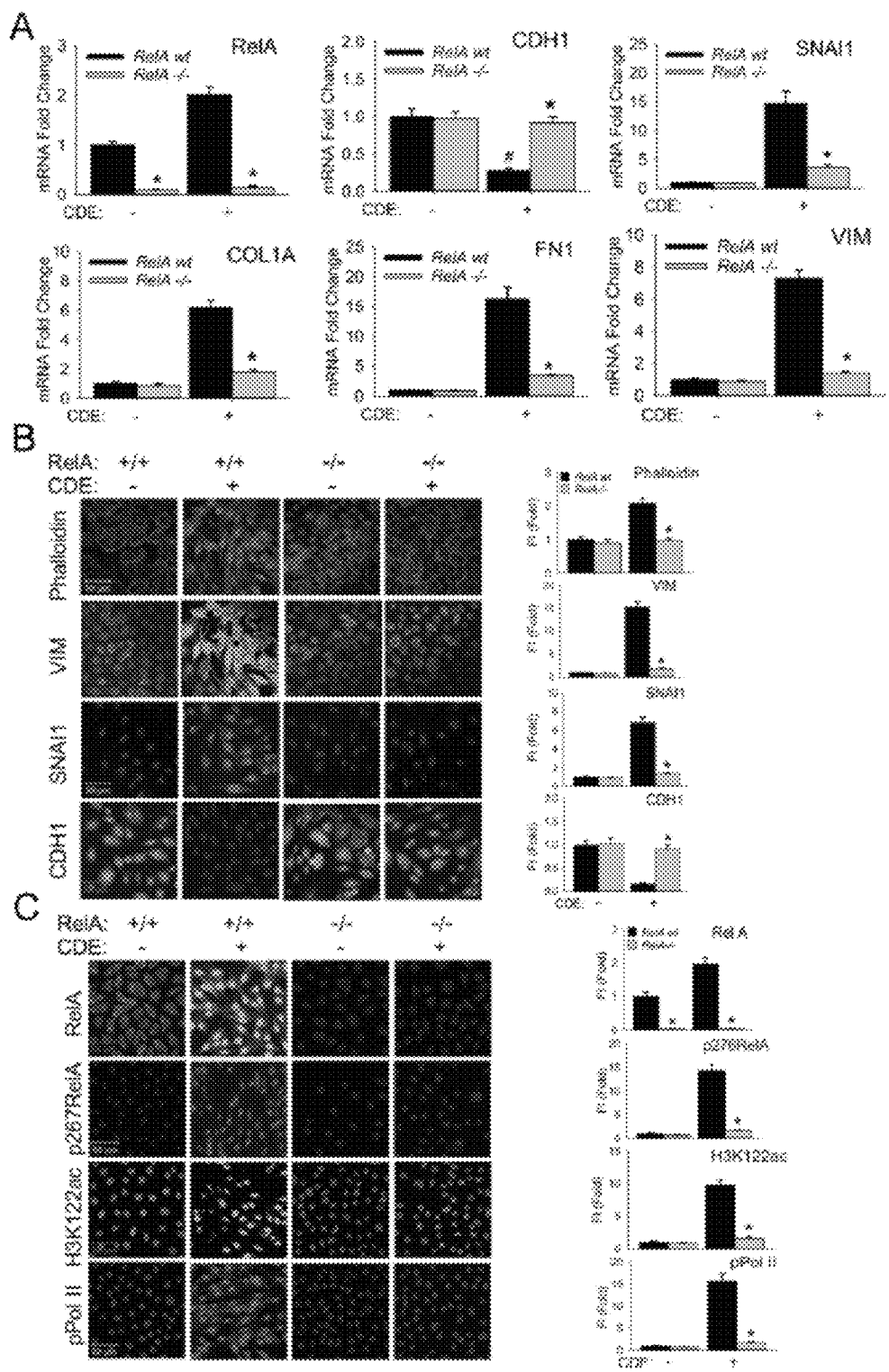
FIG. 2. NFκB/RelA mediates CDE-induced mesenchymal transition of airway epithelial cells. A, RelA shRNA-expressing hSAECs treated with/without 2 µg/ml doxycycline (Dox), 5d. Afterwards, cells were treated with CDE (20 µg/mL) for 0 or 15 d prior to analysis by Q-RT-PCR. Fold changes in indicated mRNAs are shown. * $p<0.01$ compared to control siRNA, #, $p<0.01$ compared to without CDE, n=3. B, Confocal immunofluorescence assays of WT and RelA-snRNA hSAECs. Cells were stained with either Alexa Fluor 568-conjugated phalloidin (upper panel, red color), or primary antibodies to VIM, SNAI1, and CDH1 Abs followed by secondary detection using Alexa 488-(green, for VIM and CDH1) and 568-(red, SNAI1) conjugated goat anti-rabbit IgG. Nuclei were counterstained with DAPI (blue). Images were acquired at 63× magnification. Right, quantifications of fluorescence intensities shown as fold changes compared to control hSAECs. * $p<0.01$, n=5. FI: relative total fluorescence intensity. C, Immunofluorescence assays of total RelA, phospho-Ser276 RelA, H3K122 Ac, and phospho-Ser 2 CTD Pol II (pPol II). Secondary detection was Alexa 488-(green color, for RelA and H3K122ac), and 568-(red color, for p276 RelA and pPol II) conjugated goat anti-rabbit IgG. At the right are quantifications (X±SD) of total fluorescence intensities.

The inventors next determined the role of NFκB signaling in mediating the CDE-induced mesenchymal cellular program, using hSAECs stably expressing doxycycline (Dox)-inducible RelA shRNA. Dox stimulation reduced RelA mRNA by >90% relative to that of non-Dox treated cells indicating highly effective silencing (WT, FIG. 2A).

The significant downregulation of CDH1 mRNA produced by tonic CDE stimulation was blocked in the RelA-depleted cells (FIG. 2A). Conversely, the 15-fold induction of SNAI1 mRNA produced by CDE stimulation in WT hSAECs was reduced to less than 3-fold in the RelA depleted cells. Also, RelA was similarly required for the CDE-induced 7-fold upregulation of VIM, reducing its mRNA abundance to levels similar to those of unstimulated controls (FIG. 2A). Similarly, the CDE-mediated increase of FN1 and COL1A mRNAs were significantly attenuated in the RelA depleted cells. Furthermore, the inhibition of F actin formation, VIM and SNAI1 expression and preservation of CDH1 demonstrate that NFκB/RelA is required for CDE-induced mesenchymal reprogramming (FIG. 2B).

RelA Mediates CDE-Induced BRD4 HAT and Phospho-Pol II Kinase Activities.

RelA association with BRD4 is required for the process of transcriptional elongation, promoting the TGFβ-induced mesenchymal transition program[17]. Here, Ser 276 phosphorylated RelA is acetylated by p300/CBP and bound by BRD4 through bromodomain (BD) interactions[31, 32]. Through site-specific DNA binding, RelA repositions BRD4 to the promoters of mesenchymal genes, where its intrinsic RNA Pol II kinase phosphorylates Ser 2 of the heptad repeats. Phospho Ser 2 licenses RNA Pol II to produce full-length mRNA transcripts[17, 33]. In addition, it was recently found that the association of RelA also induced the atypical HAT activity of BRD4, acetylating histone H3 on Lys (K) 122, a modification that destabilizes nucleosomes, enhancing transcription through gene bodies[25, 34]. The inventors therefore tested whether CDE stimulation activated the BRD4 HAT and/or phospho-Pol II activity and if this was RelA-dependent.

The inventors found that CDE stimulation induced a uniform translocation of the cytoplasmic RelA into the nucleus (FIG. 2C); the nuclear translocated form of RelA was serine 276 phosphorylated (FIG. 2C). The specificity of RelA and phospho-Ser 276 RelA staining was confirmed in the RelA-shRNA cells (FIG. 2C). Strikingly, CDE stimulation also induced the global accumulation of nuclear H3K122 Ac marks; this induction was RelA dependent (FIG. 2C). Similar findings were observed for the phospho-Ser 2 CTD RNA Pol II (FIG. 2C).

Repetitive CDE (rCDE) Exposures Induce an NF κB-Dependent Fibrotic Program In Vivo.

Figure 3:
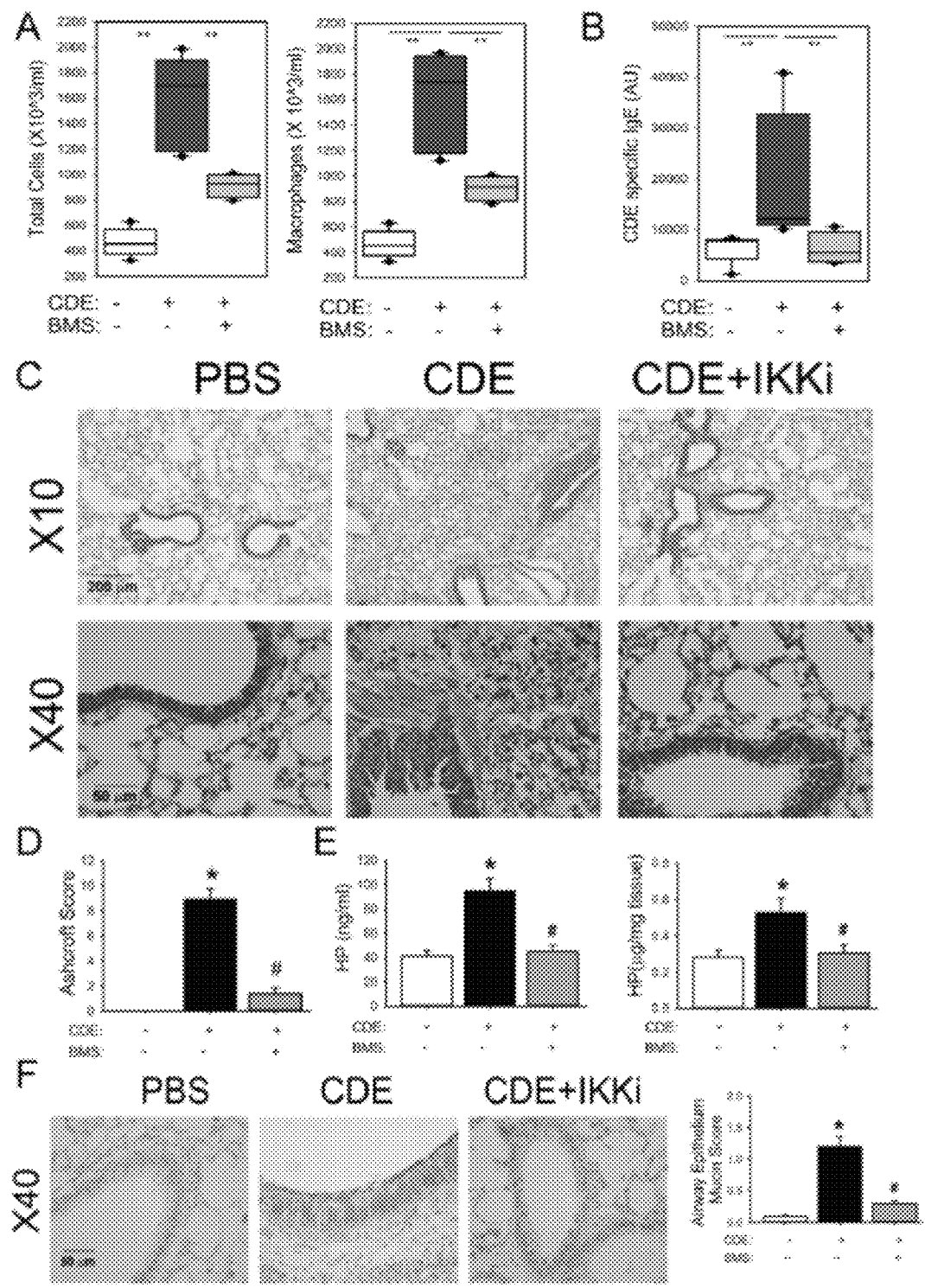
FIG. 3. Repetitive CDE (rCDE) exposure induces airway remodeling in mice. C57BL6/J mice were pretreated with and without IKK inhibitor BMS345541 and given repetitive intranasal challenges of CDE. A, Total cells and macrophages count in the bronchoalveolar lavage fluid (BALF), expressed as total number of cells×103/ml (left) and macrophages×103/ml (right). , $p<0.01$, n=5 mice per group. B, CDE specific serum IgE levels were quantitated. , $p<0.01$, n=5. C, Masson Trichrome staining of lung sections from mice in the absence (left panel) or presence of CDE (middle), or those treated with rCDE and IKK inhibitor BMS345541 (right panel). The images were taken at magnifications of 10× and 40× respectively. D, Modified Ashcroft scoring for treatment groups. *, $p<0.05$, compared to without CDE; #, $p<0.05$, compared to CDE alone. E, Quantification of hydroxyproline. Left, hydroxyproline levels in BALF. Right, hydroxyproline content in total lung tissue. *, $p<0.05$, compared to without CDE; #, $p<0.05$ compared to CDE alone. F, PAS staining (pink) by treatment groups. At right is quantification of accumulated mucin in airway epithelial cells. *, $p<0.05$, compared to without CDE; #, $p<0.05$ compared to CDE alone, n=5 mice per group.
Figure 10:
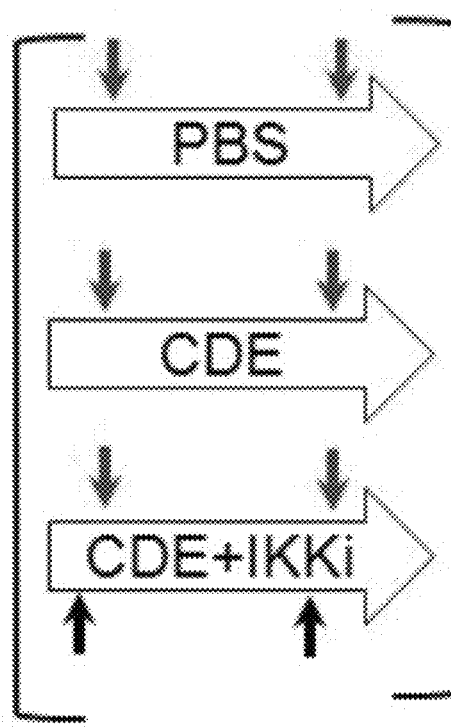
FIG. 10. Repetitive CDE (rCDE) exposure in vivo. Schematic of experimental strategy. 12 week-old C57BL/6 mice were pretreated IKK inhibitor BMS345541 (10 mg/kg body wt, ip; n=5) or vehicle and were subjected to n=15 challenges with intranasal (in) CDE (20 μg/dose) every other day for a total of 30 d. Shown is the timing of the administration for each of the treatment groups. Red vertical arrows, administration of PBS or CDE via the in route; black arrows, administration of CDE via the ip route. 12 days after the last CDE challenge, mice were sacrificed and analyzed.

To determine whether repetitive CDE exposures induce airway remodeling through the IKK-NFκB pathway, unsensitized (naïve) C57BL/6 mice were subjected to repetitive CDE exposures in the absence or presence of the selective IKK inhibitor (IKKi), BMS-345541 (BMS) 35 (see FIG. 10).

rCDE induced a 3.8-fold increase in the numbers of total leukocytes in the BALF an effect significantly reduced in the IKKi treated mice (1,700×10³ cells/ml vs 450×10³ p<0.01, ANOVA FIG. 3A). Induction of CDE-specific circulating IgE was also observed, indicating sensitization occurred during the exposure. This sensitization was completely blocked by the IKKi treatment (FIG. 3B).

Figure 11:
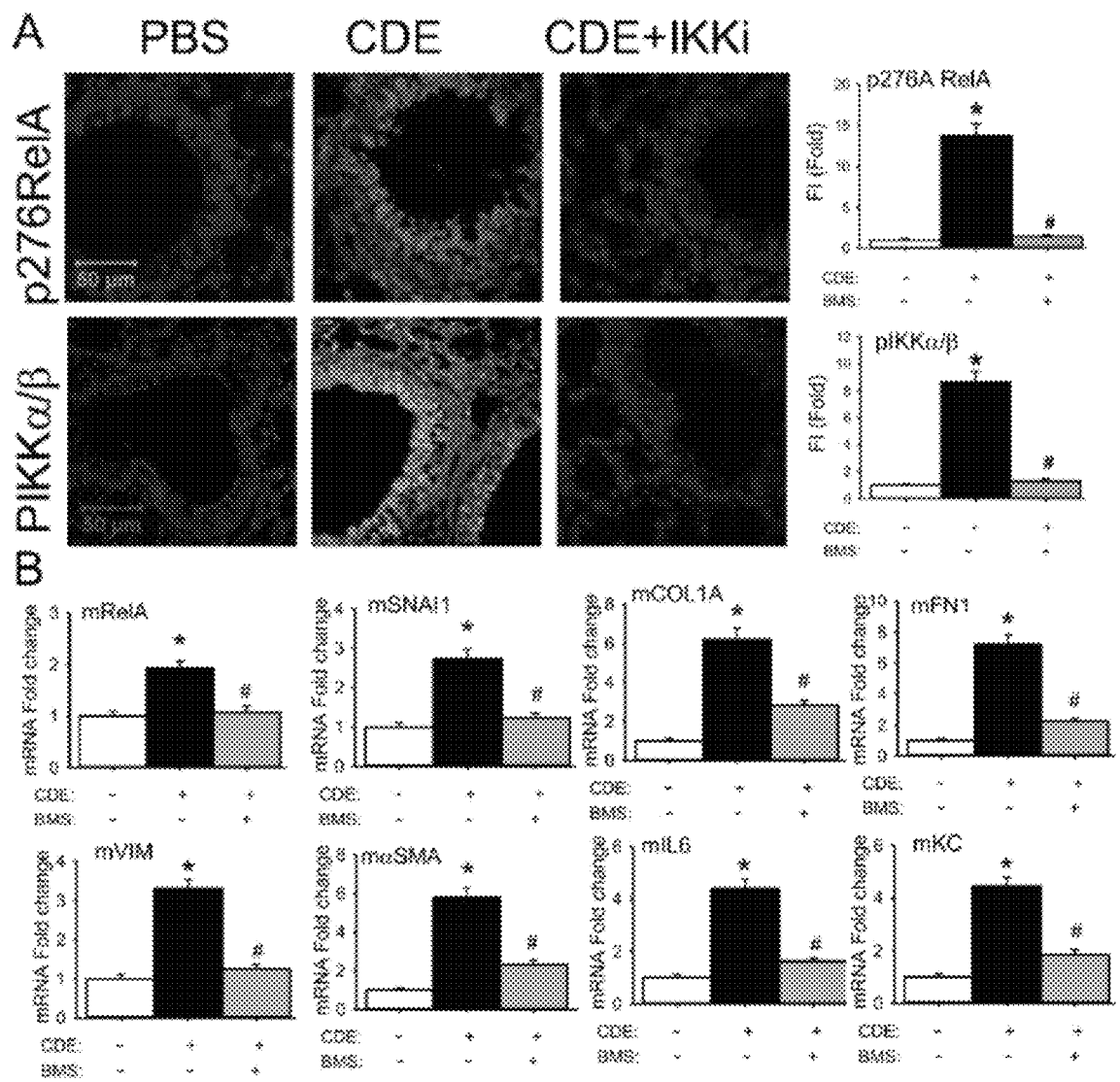
FIG. 11. rCDE exposure activates NFκB pathway and mesenchymal program in the airway mucosa. A, Confocal immunofluorescence micrographs of phospho-Ser 276 RelA (p276RelA, red) or phospho-IKK α/β, counterstained with DAPI in representative lung sections from PBS, CDE or BMS+CDE treated mice. Images were acquired at 63× magnification. At right are quantifications of relative fluorescence intensity in 5 independent images. *, $p<0.05$, compared to without CDE; #, $p<0.05$ compared to CDE alone. B, Q-RT-PCR of total RNA from lung tissues of PBS, CDE or BMS+CDE treated mice. Shown is fold change in mouse (m) mRNA expression for each gene normalized to PPIA. *, $p<0.01$, compared to without CDE; #, $p<0.01$ compared to CDE alone, n=5.

The rCDE treated lungs showed marked hypercellularity, epithelial hyperplasia, and subepithelial collagen deposition around medium sized airways, within the intersititium, and surrounding the blood vessels (FIG. 3C). Increased staining of the subepithelial fibroblast/smooth muscle cell layer was also observed. IKKi treatment reduced the fibrosis and hypercellularity, although not completely in the alveoli. A nearly 9-fold increase in the modified Ashcroft score observed in rCDE treated mice was significantly reduced in IKKi treatment group 8.8±2 vs 2±1 p<0.05, ANOVA, FIG. 3D). Additionally, rCDE stimulation produced 2-fold increase in hydroxyproline concentration in BALF and lung tissue that was normalized in the IKKi treatment group (FIG. 3E). The inventors also observed that rCDE produced a marked increase in PAS staining throughout the airway and that this effect was also blocked by the IKKi treatment (FIG. 3F). NFκB activation plays a central role in rCDE exposure-induced airway fibrosis, mucous metaplasia and remodeling.

rCDE Activates the IKK-NFκB Pathway and Mesenchymal Transition in the Airway Mucosa.

rCDE induced a 9-fold increase in phospho-IKKα/β abundance in the airway epithelial layer, an induction reduced to control values by the IKKi treatment, indicating its therapeutic effect (see FIG. 11A). The inventors also observed that rCDE exposure produced a 14-fold increase in mucosal phospho-Ser 276 RelA formation; this induction was also blocked by IKKi treatment (see FIG. 11A).

A similar induction of the mesenchymal gene expression was observed of mouse (m) RelA, α-smooth muscle actin (αSMA), SNAI1, COL1A, FN1, VIM, CXCL1/KC, and IL6 in total lung RNA extract (see FIG. 11B). This induction pattern matches the observations in the cultured hSAECs in response to tonic CDE stimulation. The induction of all of these genes were inhibited by IKKi treatment.

Figure 4:
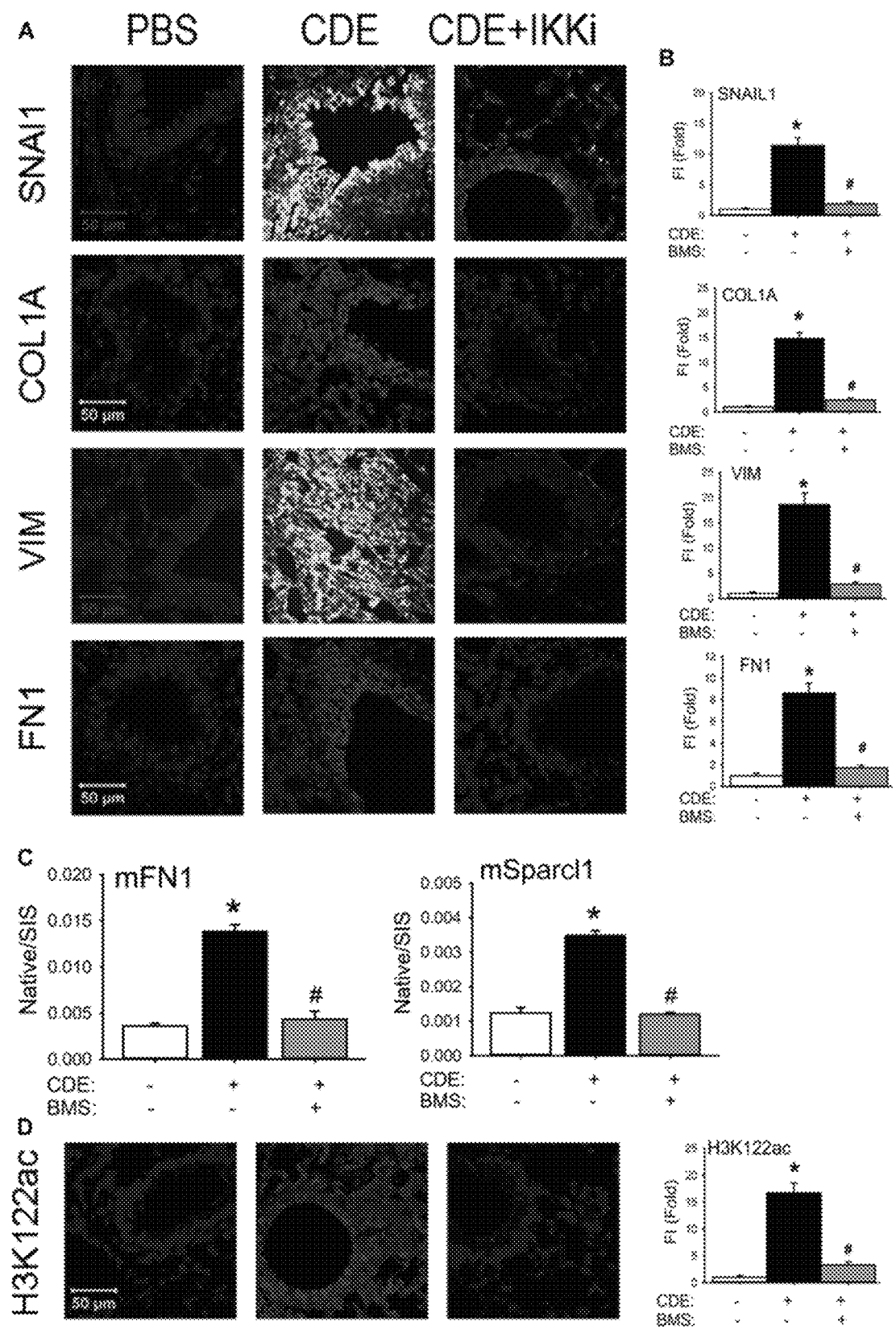
FIG. 4. rCDE induces mucosal EMT in an IKK-NF-kB-dependent manner. A, IFCM of lung sections from control (PBS-treated), CDE-treated, or BMS plus CDE-treated mice. Sections were stained for the EMT markers SNAIL VIM, COL1A, and FN1. Images are acquired at 363 magnification. B, Quantitation of relative changes in fluorescence intensity for each treatment group. *$P<0.05$ compared to without CDE and #$P<0.05$ compared to CDE alone (n 5 5), t test. C, Stable isotope dilution (SID)-SRM of the ECM proteins mFN1 and mouse Sparcl1 in BALF. Shown are means 6 SDs of native to stable isotope standards (SIS) for 5 animals in 2 technical replicates. *$P<0.05$ compared to control and #$P<0.01$ compared to CDE treatment only, t test. D, IFCM of the BRD4 activation marker H3K122Ac. Left, Quantitation of relative changes in fluorescence intensity of H3K122Ac. *$P<0.05$ compared to control and #$P<0.01$ compared to CDE treatment only, t test.

The inventors observed that rCDE exposure induced a 12-fold increase in SNAI1 expression, most intensely in the epithelium and interstitial myofibroblasts around medium- and small-sized airways (FIG. 4). Similarly, the mesenchymal intercellular contractile protein, VIM, was upregulated by 18-fold as well as the ECM proteins COL1A and FN1 (FIG. 4). Expression of these mesenchymal and ECM proteins were completely blocked in the IKKi treatment arm (FIG. 4). Collectively, these data indicate that the rCDE induces EMT in an NFκB-dependent manner.

rCDE Triggers Atypical BRD4 HAT Activity In Vivo.

Because of the strong activation of NFκB in the airway mucosa, and BRD4's dependence on NFκB activation in vitro (FIG. 2), we examined whether rCDE also stimulated the atypical BRD4 HAT activity in vivo. rCDE exposure induced a 17-fold increase in H3K122 Ac mucosal staining over that of PBS controls (FIG. 4). This pattern is similar to that of phospho-IKKα/β and phospho-Ser 276 RelA.

Myofibroblast Expansion is IKK-NFκB Pathway-Dependent.

Figure 5:
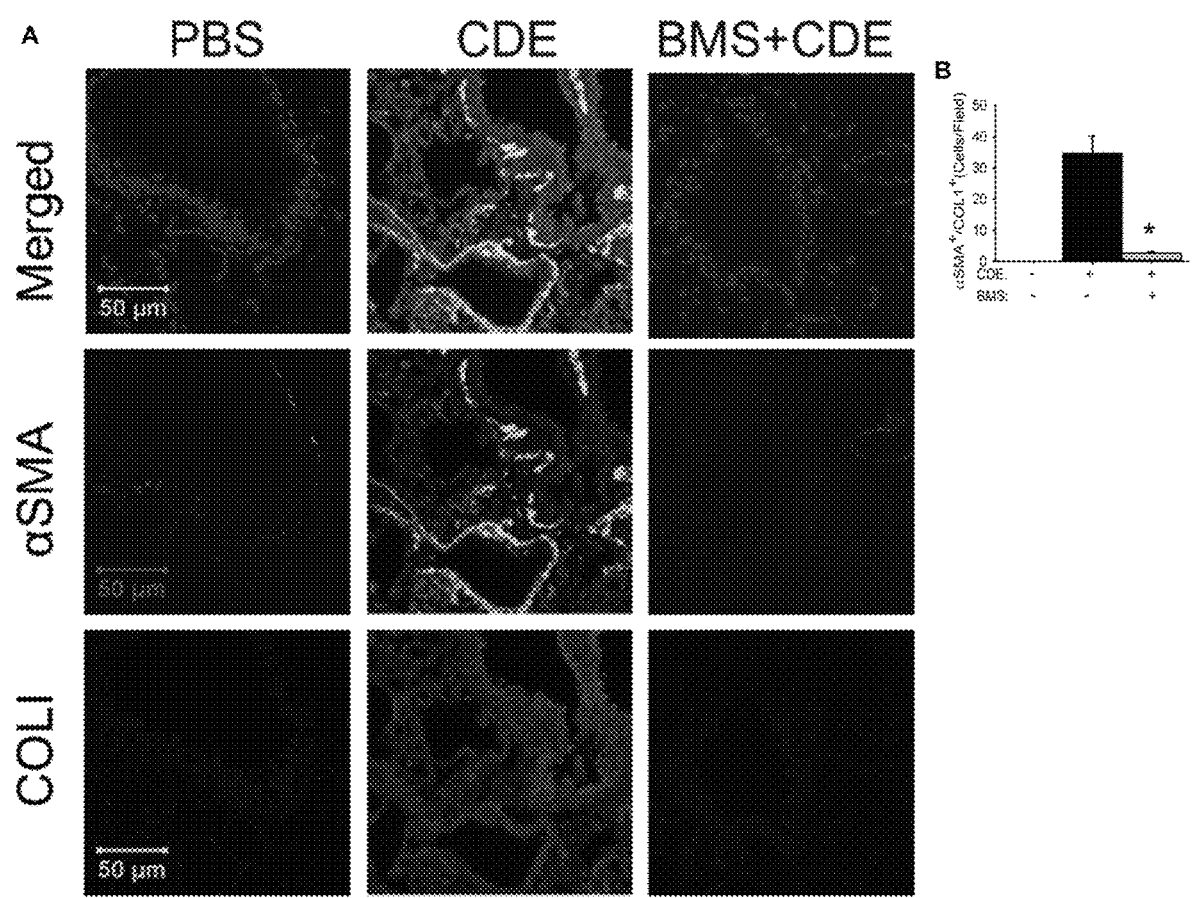
FIG. 5. rCDE induces subepithelial myofibroblast expansion. A, Confocal immunofluorescence microscopy of lung tissues in control (PBS-treated), CDE-treated, or BMS plus CDE-treated mice stained with rabbit anti-α-SMA (green color) and mouse anti-COL1 (red color) and counterstained with DAPI (blue color). Mergedimages are shown at the top (363 magnification). Experiments were independently repeated twice, with 5 animals in each treated group. B, Quantification of myofibroblasts. A total of 10 fields of each treatment were examined by 2 investigators who were blind to the treatment group (n=10). *$P<0.01$, t test.

The thickened subepithelial fibroblast layer and induction of IL6, TGFβ, and αSMA mRNAs prompted the inventors to study the myofibroblast population. The inventors observed that rCDE induced a population of αSMA+/Col1A+ myofibroblasts[36] in the subepithelial layer of small airways, a distribution consistent with the expanded fibroblast observed earlier (FIG. 5; FIG. 3C). This population was blocked by the IKKi suggesting the close inter-relationship between allergen-induced epithelial NFκB signaling, mesenchymal transition, and myofibroblast expansion.

Functional Role of BRD4 in CDE-Mediated Mesenchymal Transition of Airway Mucosa.

The inventors next tested the requirement of BRD4 HAT on rCDE-induced remodeling. For this purpose, a highly selective small molecular BRD4 antagonist was synthesized targeting the BRD4 bromodomain domain (BD) with nanomolar binding affinities and submicromolar potency. Earlier studies demonstrated that ZL0454 disrupts BRD4 binding to Pol II and histones in cellulo, releasing it from chromatin into the soluble fraction of the nucleoplasm[19].

The requirement for BRD4 on the CDE-induced mesenchymal transition was validated in hSAECs. Here, the CDE-induced inhibition of CDH1 was blocked by ZL0454 treatment (see FIG. 12A). Similarly the upregulation of SNAIL FN1, VIM, COL1A and IL6 mRNAs were all significantly blocked by ZL0454 treatment (see FIG. 12B-12D). In confocal immunofluorescence assays, ZL0454 prevented the formation of actin stress fibers, H3K122 Ac, SNAIL and VIM expression (see FIG. 12E).

Figure 12:
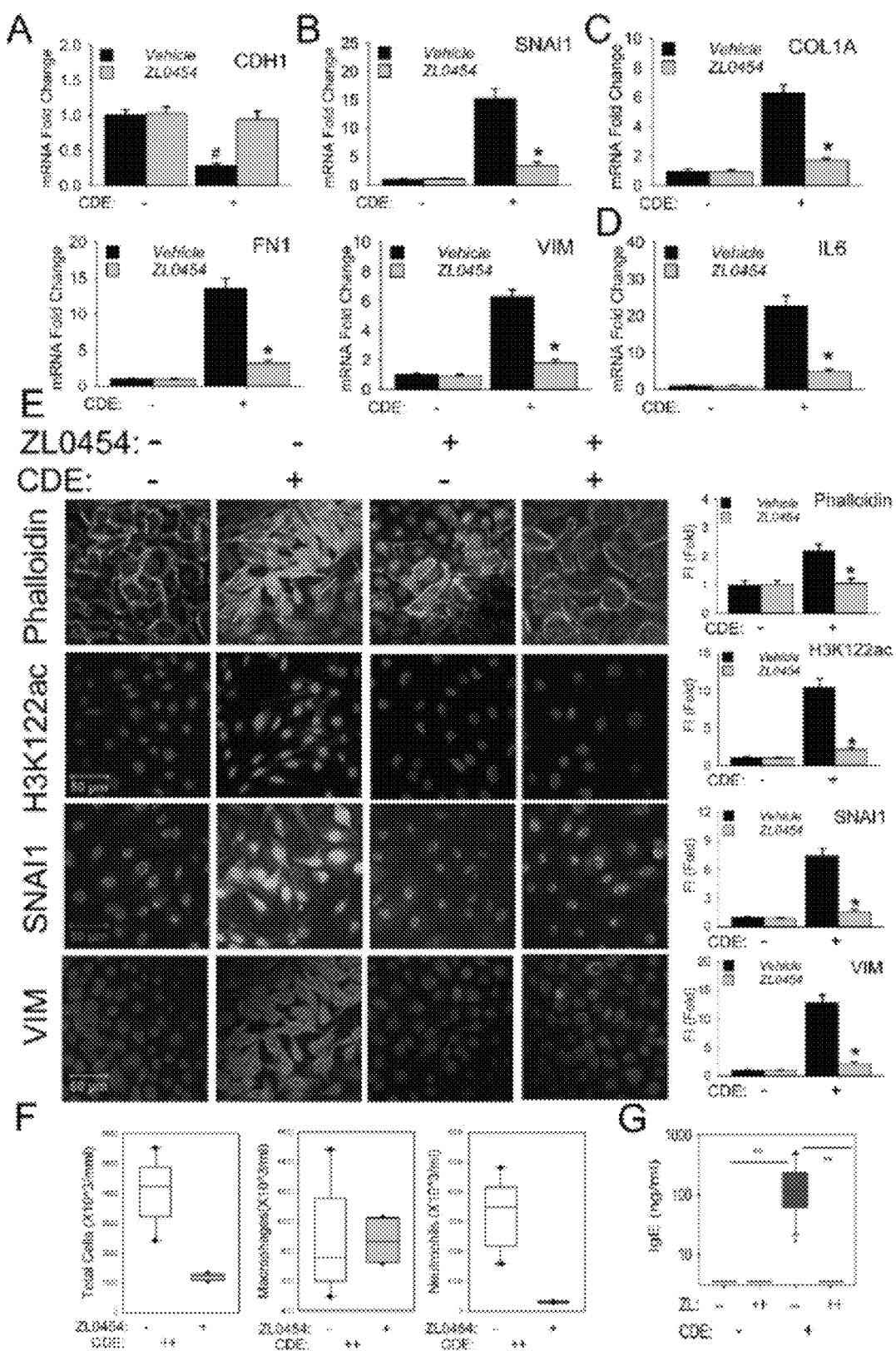
FIG. 12. BRD4 pathway mediates CDE-induced EMT of airway epithelial cells. WT hSAECs were treated with CDE (20 μg/mL) for 0 or 15 d in the presence or absence of BRD4 inhibitor ZL0454 (10 μM) before harvesting for Q-RT-PCR and performing confocal immunofluorescence microscopy. A, Q-RT-PCR for CDH1 mRNA expression. #, $p<0.01$, compared to without CDE, n=3. B, Q-RT-PCR for SNAI1 mRNA expression. *, $p<0.01$, compared to CDE alone, n=3. C, Q-RT-PCR for COL1A, FN1, and VIM mRNA expression. D, Q-RT-PCR for IL6 mRNA expression. E, Confocal immunofluorescence microscopy for phalloidin (green color), H3K122-Ac (red color), SNAI1 (green color), and VIM (red color) counterstained with DAPI (blue color) in WT hSAECs in absence or presence of CDE (20 μg/mL, 15d) stimulation. Images were acquired at 63×. At right are quantifications of relative fluorescence intensities of phalloidin, H3K122ac, SNAIL and VIM, * $p<0.01$, n=5. F, Mice were treated in absence or presence of ZL0454 (10 mg/kg) prior to acute intranasal challenge of CDE. Shown are total, macrophage, and neutrophil counts in BALF 24 h later after CDE challenge. G. Total serum IgE was quantitated for each chronic treatment group **, $p<0.01$, n=5.
Figure 13:
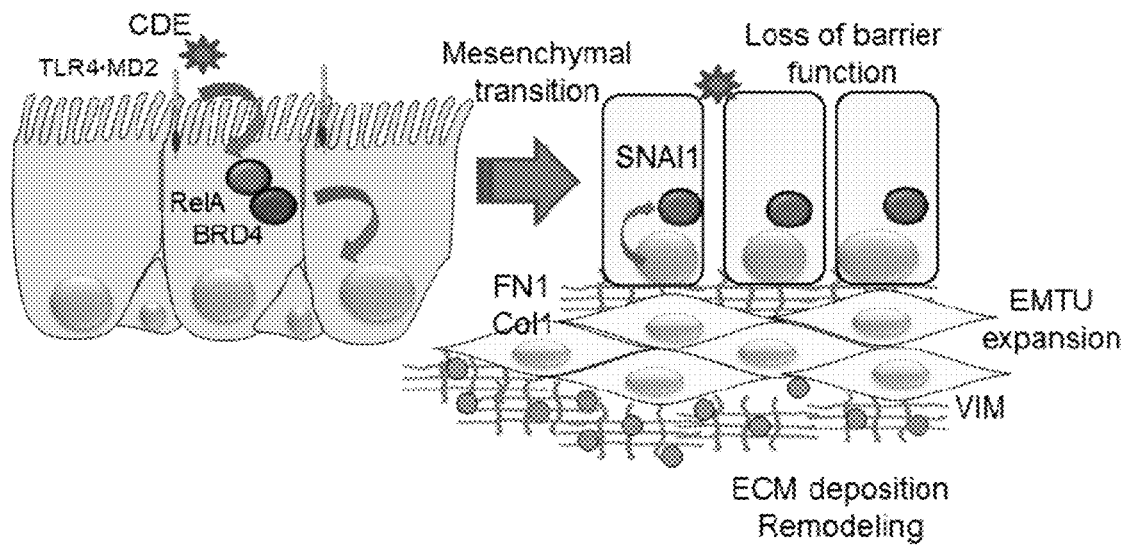
FIG. 13. E5-dependent activation of BRD4 in the epithelium is an epigenetic regulator of CDE-induced airway remodeling. Repetitive oxidative allergen cat the airway epithelial cells and upregulates its atypical histone acetyltransferase (HAT) activity. -dependent epithelial mesenchymal transition (EMT), mucous metaplasia, myofibroblast transdifferentiation, and interstitial fibrosis.

In vivo, the inventors observed that ZL0454 blocked acute CDE-induced BALF neutrophilia, observed within 24 h of treatment (see FIG. 12F). Based on this finding and earlier studies that ZL0454 is well tolerated over 3 months of administration without apparent toxicity[19], indicated that ZL0454 could be used as a probe for BRD4 actions in vivo.

rCDE-Induced Airway Fibrotic Program is Mediated by BRD4.

Figure 6:
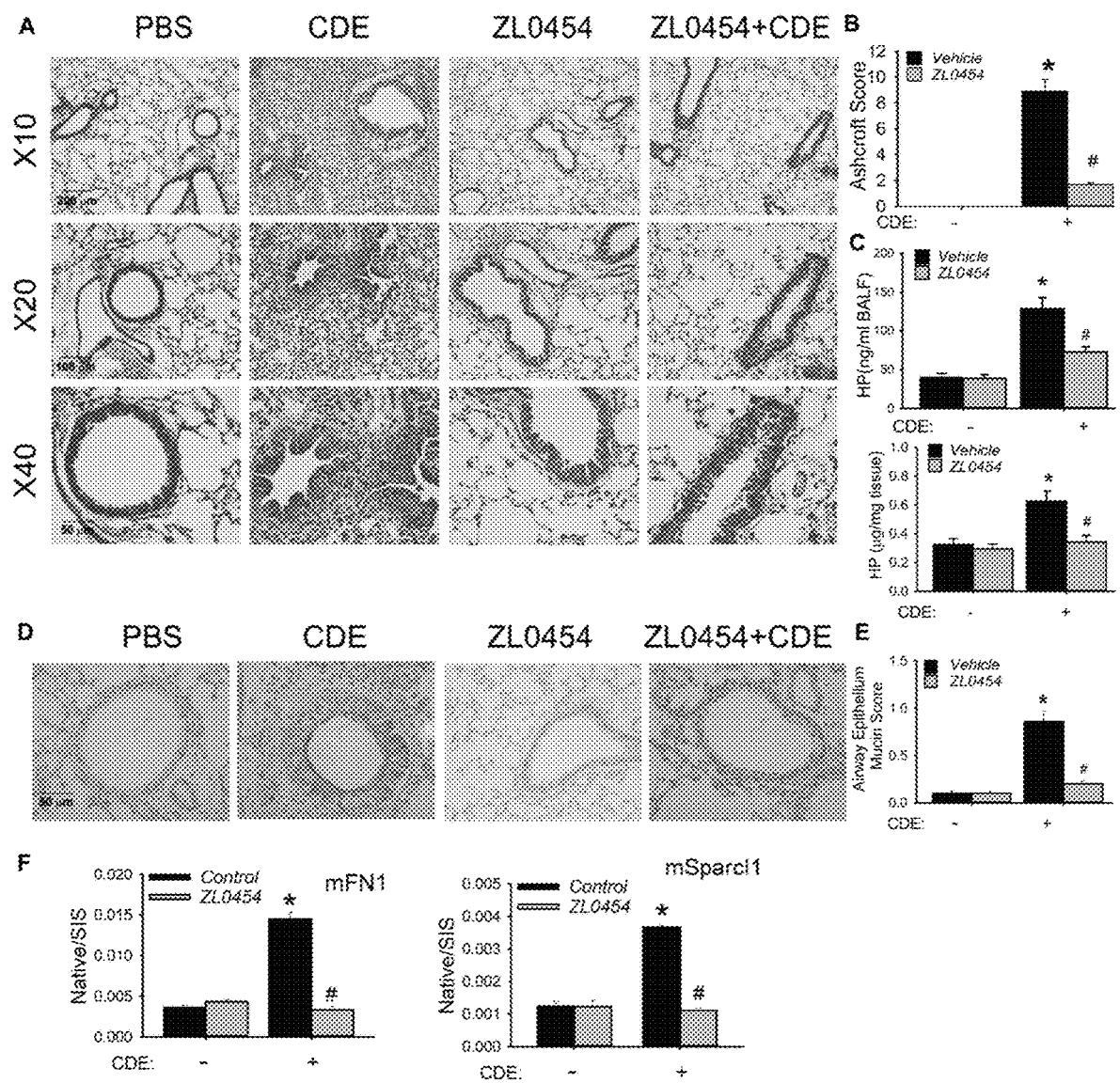
FIG. 6. BRD4 inhibitor blocks rCDE-induced airway remodeling. C57BL/6 mice were subjected to 15 treatments with PBS (administered intranasally), rCDE (20 mg/dose administered intranasally), ZL0454 (10 mg/kg body weight administered intraperitoneally), or rCDE plus ZL0454 for a total of 30 days, and lungs were harvested 12 days after the last CDE challenge. A, Masson trichrome staining at 310, 320, and 340 magnification. B, Modified Ashcroft score by treatment group. *$P<0.05$ compared to without CDE and #$P<0.05$ compared to CDE alone, t test. C, Upper, Hydroxyproline levels in BALF. Lower, Hydroxyproline content in lung tissue. *$P<0.05$ compared to without CDE and #$P<0.05$ compared to CDE alone. D, PAS staining showing mucin production. E, Quantification of cellular mucin. *$P<0.05$ compared to without CDE and #$P<0.05$ compared to CDE alone (n=5). F, Stable isotope dilution (SID)-SRM of mouse FN1 and mouse Sparcl1 in BALF. Shown are means 6 SDs of native to stable isotope standards (SIS) for 5 animals in 2 technical replicates. *$P<0.05$ compared to control and #$P<0.01$ compared to CDE treatment only, t test FIG. 7. BRD4 inhibitor blocks mucosal mesenchymal transition in vivo. A, Confocal immunofluorescence microscopy of H3K122 Ac (red color) in mouse lungs treated with PBS, rCDE, ZL0454 or rCDE+ZL0454 respectively. Lung sections were counterstained in DAPI (blue color). ×63 magnification. At the right is quantifications of relative fluorescence intensity, * $p<0.01$, n=5. B, Q-RT-PCR for mRNA expression of mesenchymal and ECM genes from total RNA of mouse lungs treated with PBS, rCDE, ZL0454 or rCDE+ZL0454. * $p<0.01$, n=5. C, Confocal immunofluorescence microscopy for SNAI1 (green color), FN1 (red color), and VIM (green color) in mouse lungs treated with PBS, rCDE, ZL0454 or rCDE+ZL0454. Lung sections were counterstained in DAPI (blue color). ×63 magnification. At right are quantitation of relative fluorescence intensities of SNAI, FN1, and VIM. *, $p<0.01$, compared to CDE alone, n=5. D, PLA assay of RelA-BRD4 molecular interactions in lung sections from PBS, rCDE, ZL0454 or rCDE+ZL0454-treated mice. Foci of interactions are amplified as red foci; sections are counterstained with DAPI (blue color). ×63 magnification. At the right is quantification of PLA assay. *, $p<0.01$, compared to CDE alone, n=5.

In the inventor's standard rCDE model, it was observed that ZL0454 treatment reduced collagen formation and hypercellularity surrounding the bronchioles and alveolar spaces (FIG. 6A). The striking Ashcroft Score of 9 produced by rCDE was reduced to 1.5 by concomitant ZL0454 treatment ($9\pm2$ vs $1.5\pm0.5$ $P<0.05$, ANOVA, FIG. 6B). Similarly, hydroxyproline content in the lung ($0.65\pm1$ vs $0.35\pm0.4$ µg/mg, FIG. 6C) and BALF ($130\pm20$ vs $70\pm10$ ng/ml, FIG. 6C) were reduced by the ZL0454 treatment. Importantly, ZL0454 also reduced the pan-epithelial mucous metaplasia in PAS staining (FIGS. 6D and 6E).

BRD4 HAT is Required for rCDE-Induced EMT.

Figure 7:
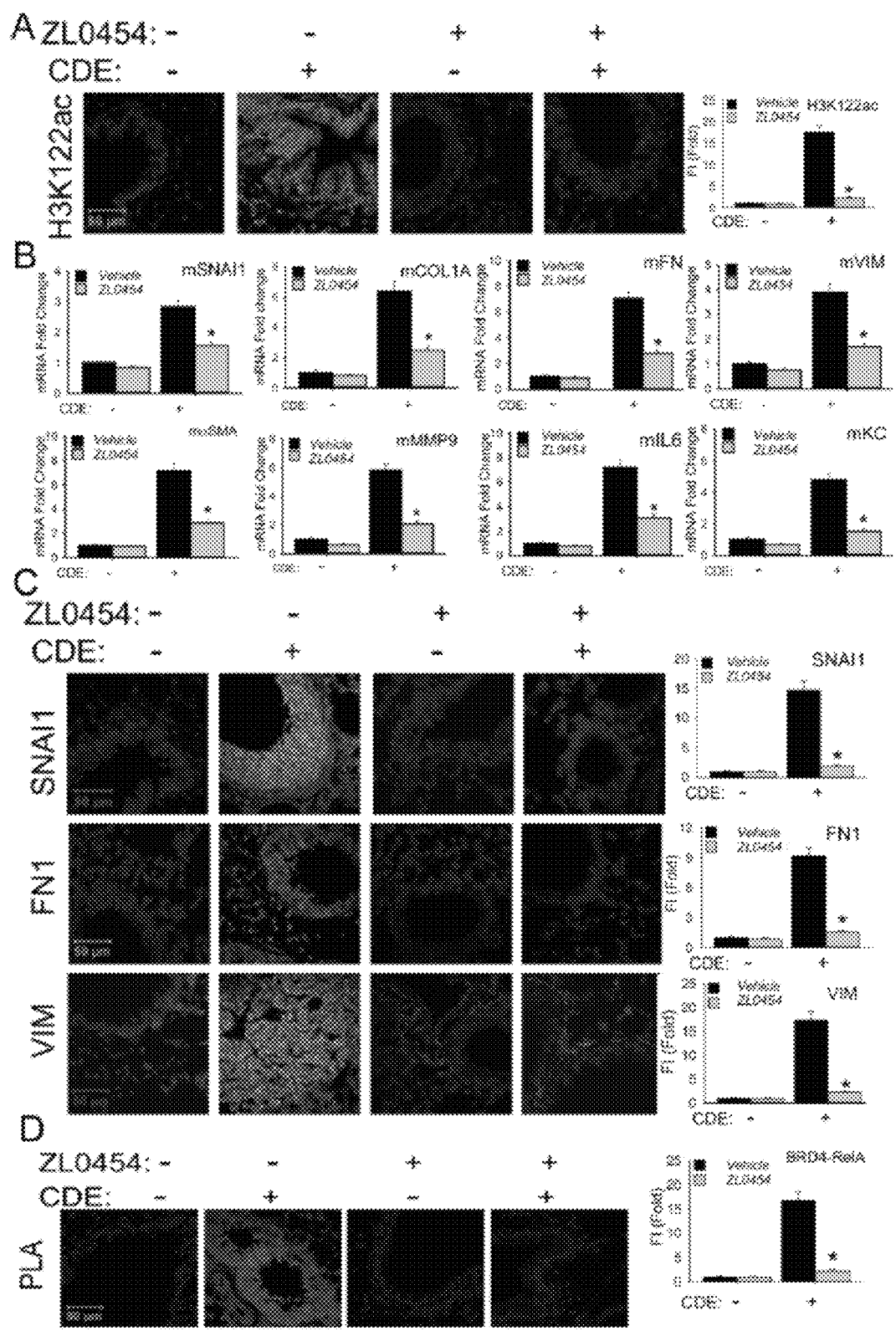

The striking induction of mucosal H3K122 Ac staining produced by rCDE was inhibited in the presence of ZL0454 (FIG. 7A), indicating that the dosing and timing of ZL0454 administration effectively inhibited BRD4 HAT in vivo. In the same tissues, the inventors observed that the rCDE-induced expression of αSMA, COL1A, FN1, VIM, and MMP9 mRNAs were BRD4-dependent (FIG. 7B). Similarly, the mucosal induction of SNAI1, FN1, and VIM observed in immunofluorescence microscopy was also inhibited by ZL0454 treatment (FIG. 7C).

Activated RelA binds to BRD4[25, 31], an interaction mediated by the BRD4 BD domain, a target of ZL0454[19]. To measure this molecular interaction in the airway mucosa, the inventors applied a proximity ligation assay (PLA), an assay that detects atomic-distance interactions between two molecules[37]. After heterotypic Ab staining, oligonucleotide ligation and PCR amplification, RelA-BRD4 interactions appear as fluorescent foci in situ[25]. The inventors observed that the rCDE-induced molecular RelA.BRD4 binding was disrupted by ZL0454 treatment (FIG. 7D).

rCDE Induced Myofibroblast Expansion is BRD4 Dependent.

Figure 8:
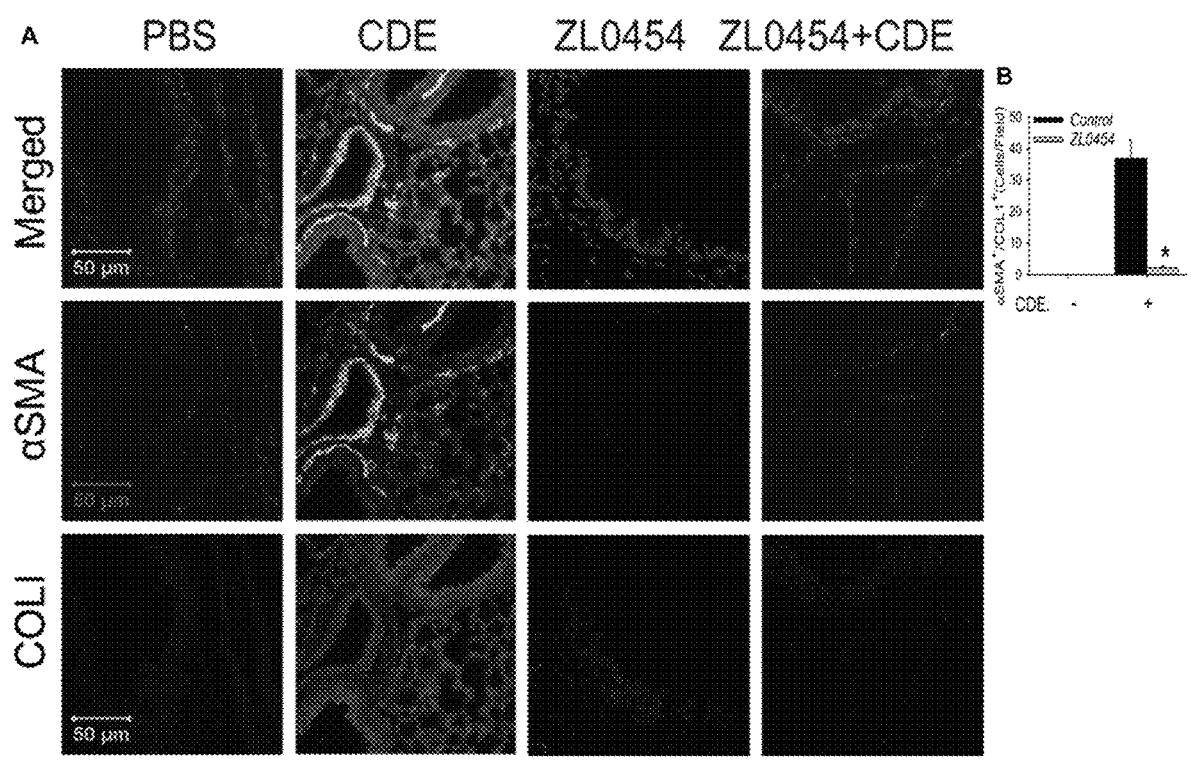
FIG. 8. BRD4 mediates allergen-induced myofibroblast transition. A, Confocal immunofluorescence microscopy of lung sections in PBS-, rCDE-, ZL0454-, or rCDE plus ZL0454-treated mice stained with both primary antibodies of rabbit anti-α-SMA and mouse anti-COL1 antibodies and counterstained with DAPI. Merged images are shown at top (363 magnification). Experiments were independently repeated twice, with 5 animals in each treated group. B, Quantification of myofibroblasts. A total of 10 fields of each treatment were examined by 2 investigators who were blind to the treatment group (n=10). *$P<0.01$, t test.

Finally, the inventors found that activation of the subepithelial αSMA+/COL1+ co-staining myofibroblast cells by rCDE was also blocked by ZL0454 treatment (FIG. 8), indicating that the allergen induced mucosal NFκB-BRD4 signaling affects airway remodeling through its direct effects on epithelial cell state, growth factor and ECM production, indirectly producing expansion of subepithelial myofibroblasts.

REFERENCES

1. Broide D H. J Allergy Clin Immunol 2008; 121:560-70; quiz 71-2.
2. Pawankar R. World Allergy Organ J 2014; 7:12.
3. Dahl R, Andersen P S, Chivato T, Valovirta E, de Monchy J. Respir Med 2004; 98:398-403.
4. Prakash Y S, Halayko A J, Gosens R, Panettieri R A, Jr., Camoretti-Mercado B, Penn R B, et al. Am J Respir Crit Care Med 2017; 195:e4-e19.
5. Hosoki K, Aguilera-Aguirre L, Brasier A R, Kurosky A, Boldogh I, Sur S. Am J Respir Cell Mol Biol 2016; 54:81-90.
6. Hosoki K, Boldogh I, Aguilera-Aguirre L, Sun Q, Itazawa T, Hazra T, et al. J Allergy Clin Immunol 2016; 137:1506-13.e2.
7. Arizmendi N G, Abel M, Mihara K, Davidson C, Polley D, Nadeem A, et al. J Immunol 2011; 186:3164-72.
8. Kale S L, Agrawal K, Gaur S N, Arora N. Sci Rep 2017; 7:42341.
9. Kheradmand F, Kiss A, Xu J, Lee S H, Kolattukudy P E, Corry D B. J Immunol 2002; 169:5904-11.
10. Hammad H, Lambrecht B N. Nat Rev Immunol 2008; 8:193-204.
11. Salo P M, Arbes S J, Jr., Jaramillo R, Calatroni A, Weir C H, Sever M L, et al. J Allergy Clin Immunol 2014; 134:350-9.
12. Kelly L A, Erwin E A, Platts-Mills T A. Curr Opin Pulm Med 2012; 18:29-34.
13. Hosoki K, Redding D, Itazawa T, Chakraborty A, Tapryal N, Qian S, et al. J Allergy Clin Immunol 2017.
14. Kalita M, Tian B, Gao B, Choudhary S, Wood T G, Carmical J R, et al. BioMed Research International 2013; 2013:505864.
15. Tian B, Li X, Kalita M, Widen S G, Yang J, Bhavnani S K, et al. BMC Genomics 2015; 16:529.
16. Tian B, Patrikeev I, Ochoa L, Vargas G, Belanger K K, Litvinov J, et al. Am J Respir Cell Mol Biol 2016.
17. Tian B, Zhao Y, Sun H, Zhang Y, Yang J, Brasier A R. The American Journal of Physiology—Lung Cellular and Molecular Physiology 2016; 311:L1183-L201.
18. Zhao Y, Tian B, Sadygov R G, Zhang Y, Brasier A R. J Proteomics 2016; 148:126-38.
19. Tian B, Liu Z, Yang J, Sun H, Zhao Y, Wakamiya M, et al. Cell Reports 2018; in press.
20. Lambrecht B N, Hammad H. Nat Med 2012; 18:684-92.
21. Holgate S T, Holloway J, Wilson S, Bucchieri F, Puddicombe S, Davies D E. Proc Am Thorac Soc 2004; 1:93-8.
22. Rock J R, Barkauskas C E, Cronce M J, Xue Y, Harris J R, Liang J, et al. Proc Natl Acad Sci USA 2011; 108:E1475-83.
23. Ijaz T, Pazdrak K, Kalita M, Konig R, Choudhary S, Tian B, et al. World Allergy Organization Journal 2014; 7:13.
24. Zhao Y, Jamaluddin M, Zhang Y, Sun H, Ivanciuc T, Garofalo R P, et al. J Immunol 2017; 198:3345-64.
25. Tian B, Yang J, Zhao Y, Ivanciuc T, Sun H, Garofalo R P, et al. Journal of Virology 2017; 91:doi: 10.1128/JVI.00007-17
26. Ramirez R D, Sheridan S, Girard L, Sato M, Kim Y, Pollack J, et al. Cancer Res 2004; 64:9027-34.
27. Chang H, Liu Y, Xue M, Liu H, Du S, Zhang L, et al. Nucleic Acids Res 2016; 44:2514-27.
28. Amara N, Goven D, Prost F, Muloway R, Crestani B, Boczkowski J. Thorax 2010; 65:733-8.
29. Hiraga R, Kato M, Miyagawa S, Kamata T. Anticancer Research 2013; 33:4431-8.
30. Wu R F, Ma Z, Liu Z, Terada L S. Mol Cell Biol 2010; 30:3553-68.
31. Brasier A R, Tian B, Jamaluddin M, Kalita M K, Garofalo R P, Lu M. J Virol 2011; 85:11752-69.

32. Huang B, Yang X D, Zhou M M, Ozato K, Chen Lf. Molecular and Cellular Biology 2009; 29:1375-87.
33. Tian B, Zhao Y, Kalita M, Edeh C B, Paessler S, Casola A, et al. J Virol 2013; 87:7075-92.
34. Devaiah B N, Case-Borden C, Gegonne A, Hsu C H, Chen Q, Meerzaman D, et al. Nat Struct Mol Biol 2016; 23:540-8.
35. Burke J R, Pattoli M A, Gregor K R, Brassil P J, MacMaster J F, McIntyre K W, et al. Journal of Biological Chemistry 2003; 278:1450-6.
36. Ijaz T, Jamaluddin M, Zhao Y, Zhang Y, Finnerty C C, Jay J, et al. Cell Death Differ 2017; 8(2)::e2606.
37. Hammond M, Nong R Y, Ericsson O, Pardali K, Landegren U. PLoS ONE 2012; 7:e40405.
38. Ather J L, Hodgkins S R, Janssen-Heininger Y M W, Poynter M E. American Journal of Respiratory Cell and Molecular Biology 2011; 44:631-8.
39. Tully J E, Hoffman S M, Lahue K G, Nolin J D, Anathy V, Lundblad L K A, et al. The Journal of Immunology 2013.
40. Kale S L, Arora N. Immunobiology 2015; 220:525-32.
41. Chua H L, Bhat-Nakshatri P, Clare S E, Morimiya A, Badve S, Nakshatri H. Oncogene 2007; 26:711-24.
42. Batlle E, Sancho E, Franci C, Dominguez D, Monfar M, Baulida J, et al. Nat Cell Biol 2000; 2:84-9.
43. Al-Muhsen S, Johnson J R, Hamid Q. J Allergy Clin Immunol 2011; 128:451-62; quiz 63-4.
44. Brewster C E P, Howarth P H, Djukanovic R, Wilson J, Holgate S T, Roche W R. American Journal of Respiratory Cell and Molecular Biology 1990; 3:507-11.
45. Fedorov I A, Wilson S J, Davies D E, Holgate S T. Thorax 2005; 60:389-94.
46. Bergeron C, Tulic M K, Hamid Q. Can Respir J 2010; 17:e85-93.
47. Boser S R, Mauad T, de Araújo-Paulino B B, Mitchell I, Shrestha G, Chiu A, et al. PLoS ONE 2017; 12:e0182378.
48. Carroll N G, Perry S, Karkhanis A, Harji S, Butt J, James A L, et al. Am J Respir Crit Care Med 2000; 161:244-8.
49. Bentley J K, Popova A P, Bozyk P D, Linn M J, Baek A E, Lei J, et al. Respiratory Research 2010; 11:127-.
50. Ray S, Ju X, Sun H, Finnerty C C, Herndon D N, Brasier A R. J Invest Dermatol 2013; 133:1212-20.
51. Liu Z, Wang P, Chen H, Wold E, Tian B, Brasier A R, et al. Journal of Medical Chemistry 2017; 60:4533-58.
52. Devaiah B N, Lewis B A, Cherman N, Hewitt M C, Albrecht B K, Robey P G, et al. Proc Natl Acad Sci USA 2012; 109:6927-32.
53. Brown J D, Lin C Y, Duan Q, Griffin G, Federation A J, Paranal R M, et al. Mol Cell 2014; 56:219-31.
54. Zhang Y, Sun H, Zhang J, Brasier A R, Zhao Y. Journal of Proteome Research 2017; in press.
55. Naclerio R M, Meier H L, Kagey-Sobotka A, Adkinson N F, Jr., Meyers D A, Norman P S, Lichtenstein L M. Am Rev Respir Dis. 1983; 128(4):597-602. doi: 10.1164/arrd.1983.128.4.597. PubMed PMID: 6354022.
56. Creticos P S, Peters S P, Adkinson N F, Jr., Naclerio R M, Hayes E C, Norman P S, Lichtenstein L M. N Engl J Med. 1984; 310(25):1626-30. doi: 10.1056/NEJM198406213102502. PubMed PMID: 6328300.
57. Creticos P S, Adkinson N F, Jr., Kagey-Sobotka A, Proud D, Meier H L, Naclerio R M, Lichtenstein L M, Norman P S. The Journal of clinical investigation. 1985; 76(6): 2247-53. Epub 1985/12/01. doi: 10.1172/JCI112233. PubMed PMID: 2416777; PMCID: 424347.
58. Peters-Golden M, Gleason M M, Togias A. Clin Exp Allergy. 2006; 36(6):689-703. doi: 10.1111/j.1365-2222.2006.02498.x. PubMed PMID: 16776669; PMCID: PMC1569601.
59. Navin, #xe9, s-Ferrer A, Serrano-Candelas E, Molina-Molina G-J, Mart, #xed, n. Journal of Immunology Research. 2016; 2016:12. doi: 10.1155/2016/8163803.
60. Pawankar R. World Allergy Organ J. 2014; 7(1):12. doi: 10.1186/1939-4551-7-12. PubMed PMID: 24940476; PMCID: PMC4045871.
61. Singh K, Axelrod S, Bielory L. The Journal of allergy and clinical immunology. 2010; 126(4):778-83 e6. doi: 10.1016/j.jaci.2010.06.050. PubMed PMID: 20920769.
62. Arbes S J, Jr., Gergen P J, Vaughn B, Zeldin D C. The Journal of allergy and clinical immunology. 2007; 120 (5):1139-45. Epub 2007/09/25. doi: 10.1016/j.jaci.2007.07.056. PubMed PMID: 17889931; PMCID: 2291202.
63. Lamb C E, Ratner P H, Johnson C E, Ambegaonkar A J, Joshi A V, Day D, Sampson N, Eng B. Curr Med Res Opin. 2006; 22(6):1203-10. doi: 10.1185/030079906X112552. PubMed PMID: 16846553.
64. Akinbami L J, Moorman J E, Bailey C, Zahran H S, King M, Johnson C A, Liu X. NCHS data brief 2012(94):1-8. PubMed PMID: 22617340.
65. Busse W W, Lemanske R F. New England Journal of Medicine. 2001; 344:350-62.
66. Lloyd A, Price D, Brown R. Primary Care Respiratory Journal. 2007; 16:22. doi: 10.3132/perj 0.2007.00002.
67. Nowak-Wegrzyn A, Szajewska H, Lack G. Nature Reviews Gastroenterology &Amp; Hepatology. 2016; 14:241. doi: 10.1038/nrgastro.2016.187.
68. Hosoki K, Aguilera-Aguirre L, Brasier A R, Kurosky A, Boldogh I, Sur S. Am J Respir Cell Mol Biol. 2016; 54(1):81-90. doi: 10.1165/rcmb.2015-0044OC. PubMed PMID: 26086549; PMCID: PMC4742928.
69. Hosoki K, Boldogh I, Aguilera-Aguirre L, Sun Q, Itazawa T, Hazra T, Brasier A R, Kurosky A, Sur S. The Journal of allergy and clinical immunology. 2016; 137 (5):1506-13.e2. Epub 2015/11/21. doi: 10.1016/j.jaci.2015.09.036. PubMed PMID: 26586036; PMCID: PMC4860180.
70. Hosoki K, Redding D, Itazawa T, Chakraborty A, Tapryal N, Qian S, Qi H, Aguilera-L, Aguirre, Hazra T, Boldogh I, sur s. The Journal of allergy and clinical immunology. 2017; Accepted.
71. Pelikan Z. Am J Rhinol Allergy. 2013; 27(5):345-53. doi: 10.2500/ajra.2013.27.3933. PubMed PMID: 24119599.
72. Fransson M, Benson M, Wennergren G, Cardell L O. Acta Otolaryngol. 2004; 124(5):616-20. PubMed PMID: 15267182.
73. Miadonna A, Milazzo N, Gibelli S, Salmaso C, Lorini M, Tedeschi A. Clin Exp Allergy. 1999; 29(7):941-9. PubMed PMID: 10383595.
74. Tian B, Liu Z, Yang J, Sun H, Zhao Y, Wakamiya M, et al. Cell Reports 2018; in press.
75. Tian B, Patrikeev I, Ochoa L, Vargas G, Belanger K K, Litvinov J, et al. Am J Respir Cell Mol Biol 2016.
76. Hosoki K, Aguilera-Aguirre L, Brasier A R, Kurosky A, Boldogh I, Sur S. Am J Respir Cell Mol Biol 2016; 54:81-90.
77. Hosoki K, Boldogh I, Aguilera-Aguirre L, Sun Q, Itazawa T, Hazra T, et al. J Allergy Clin Immunol 2016; 137:1506-13.e2.
78. Tian B, Zhao Y, Sun H, Zhang Y, Yang J, Brasier A R. The American Journal of Physiology—Lung Cellular and Molecular Physiology 2016; 311:L1183-L201.

79. Tian B, Li X, Kalita M, Widen S G, Yang J, Bhavnani S K, et al. BMC Genomics 2015; 16:529.
80. Tian B, Zhao Y, Kalita M, Edeh C B, Paessler S, Casola A, et al. J Virol 2013; 87:7075-92.

The invention claimed is:

1. A method for treating or ameliorating one or more clinical features of airway remodeling due to an IgE-mediated disease, comprising: administering to a subject having or at risk of developing one or more clinical features of airway remodeling due to an IgE-mediated disease an effective amount of a small molecule BRD4 inhibitor selected from the group consisting of ZL0420, ZL0454, ZL0556, ZL0586, ZL0590, ZL0591, ZL0589, ZL0468, ZL0513, ZL0516, and ZL0165.

2. The method of claim 1, wherein the small molecule BRD4 inhibitor is administered at 0.1 to 100 mg/kg body weight.

3. A method for treating or ameliorating one or more clinical features of airway remodeling due to allergic asthma or severe asthma with elevated IgE, comprising: administering to a subject having or at risk of developing one or more clinical features of airway remodeling due to allergic asthma or severe asthma with elevated IgE an effective amount of a small molecule BRD4 inhibitor selected from the group consisting of ZL0420, ZL0454, ZL0556, ZL0586, ZL0590, ZL0591, ZL0589, ZL0468, ZL0513, ZL0516, and ZL0165.

4. The method of claim 3, wherein the small molecule BRD4 inhibitor is administered at 0.1 to 100 mg/kg body weight.

5. The method of claim 1, wherein the one or more clinical features is fibrosis, mucous metaplasia, barrier disruption from epithelial mesenchymal transition (EMT), vascular remodeling or angiogenesis, airway hyper-responsiveness, or any combinations thereof.

6. The method of claim 1, wherein the BRD4 inhibitor is ZL0454.

7. The method of claim 3, wherein the one or more clinical features is fibrosis, mucous metaplasia, barrier disruption from epithelial mesenchymal transition (EMT), vascular remodeling or angiogenesis, airway hyper-responsiveness, allergic sensitization, or IgE production to cat aeroallergen, or any combinations thereof.

8. The method of claim 3, wherein the BRD4 inhibitor is ZL0454.

* * * * *